US 9,562,010 B2

(12) United States Patent
Gunawardena et al.

(10) Patent No.: US 9,562,010 B2
(45) Date of Patent: Feb. 7, 2017

(54) CROSS-LINKING COMPOSITIONS AND RELATED METHODS OF ISOTOPE TAGGING OF INTERACTING PROTEINS AND ANALYSIS OF PROTEIN INTERACTIONS

(71) Applicant: The University of North Carolina at Chapel Hill, Chapel Hill, NC (US)

(72) Inventors: Harsha P. Gunawardena, Raleigh, NC (US); Xian Chen, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 113 days.

(21) Appl. No.: 14/161,294

(22) Filed: Jan. 22, 2014

(65) Prior Publication Data
US 2014/0206091 A1 Jul. 24, 2014

Related U.S. Application Data

(60) Provisional application No. 61/755,282, filed on Jan. 22, 2013.

(51) Int. Cl.
*C07D 207/416* (2006.01)
*G01N 33/68* (2006.01)

(52) U.S. Cl.
CPC ....... *C07D 207/416* (2013.01); *G01N 33/6851* (2013.01)

(58) Field of Classification Search
CPC .............................................. C07D 207/416
See application file for complete search history.

(56) References Cited

U.S. PATENT DOCUMENTS 5,652,347 A * 7/1997 Pouyani .............. C08B 37/0072
536/123.1

OTHER PUBLICATIONS

Ahrman, E., Lambert, W., Aquilina, J.A,. Robinson, C.V. & Emanuelsson, C.S Chemical cross-linking of the chloroplast localized small heat-shock protein, Hsp21, and the model substrate citrate synthase. Protein science :a publication of the Protein Society 16, 1464-1478 (2007).
Agarwal, A.; Diedrich, J.K.; Julian, R.R., Direct elucidation of disulfide bond partners using ultraviolet photodissociation mass spectrometry. Anal chem 2011, 83, (17), 6455-8.
Bennett, K.L. et al. Chemical cross-linking with thiol-cleavable reagents combined with differential mass spectrometric peptide mapping—a novel approach to assess intermolecular protein contacts. Protein science :a publication of the Protein Society 9, 1503-1518 (2000).
Chrisman, P.A.; McLuckey, S.A., Dissociations of disulfide-linked gaseous polypeptide/protein anions: ion chemistry with implications for protein identification and characterization. J Proteome Res 2002, 1, (6), 549-57.
Chrisman, P. A.; Pitteri, S. J.; Hogan, J. M.; McLuckey, S. A., SO2-* electron transfer ion/ion reactions with disulfide linked polypeptide ions. J Am Soc Mass Spectrom 2005, 16, (7), 1020-30.
Elias, J. E.; Gygi, S. P., Target-decoy search strategy for increased confidence in large-scale protein identifications by mass spectrometry. Nat Methods 2007, 4, (3), 207-14.
Frankevich, V.; Zhang, J.; Dashtiev, M.; Zenobi, R., Production and fragmentation of multiply charged ions in 'electron-free' matrix-assisted laser desorption/ionization. Rapid Common Mass Spectrom 2003, 17, (20), 2343-8.
Fukuyama, Y.; Iwamoto, S.; Tanaka, K., Rapid sequencing and disulfide mapping of peptides containing disulfide bonds by using 1,5-diaminoaphthalene as a reductive matrix. J Mass Spectrom 2006, 41, (2), 191-201.
Gardner, M. W.; Brodbelt, J. S., Preferential cleavage of N—N hydrazone bonds for sequencing bis-arylhydrazone conjugated peptides by electron transfer dissociation. Anal Chem 2010, 82, (13), 5751-9.
Gao, Q. et al. Minimize the detection of false positives by the software program DetectShift for 18O-labeled cross-linked peptide analysis. Eur J Mass Spectrom (Chichester, Eng) 14, 275-280 (2008).
Gunawardena, H. P.; He, M.; Chrisman, P. A.; Pitteri, S. J.; Hogan, J. M.; Hodges, B. D.; McLuckey, S. A., Electron transfer versus proton transfer in gas-phase ion/ion reactions of polyprotonated peptides. J Am Chem Soc 2005, 127, (36), 12627-39.
Gunawardena, H.P.; O'Hair, R.A.; McLuckey, S.A., Selective disulfide bond cleavage in gold(I) cationized polypeptide ions formed via gas-phase ion/ion cation switching. J Proteome Res 2006, 5, (9), 2087-92.
Gunawardena, H. P.; Huang, Y.; Kenjale, R.; Wang, H.; Xie, L.; Chen, X., Unambiguous characterization of site-specific phosphorylation of leucine-rich repeat Fli-I-interacting protein 2 (LRRFIP2) in Toll-like receptor 4 (TLR4)-mediated signaling. J Biol Chem 2011, 286, (13), 10897-910.
Hoopmann, M. R.; Weisbrod, C. R.; Bruce, J. E., Improved strategies for rapid identification of chemically cross-linked peptides using protein interaction reporter technology. J Proteome Res 2010, 9, (12), 6323-33.
Kalkhof, S. & Sinz, A. Chances and pitfalls of chemical cross-linking with amine-reactive N-hydroxysuccinimide esters. Analytical and bioanalytical chemistry 392, 305-312 (2008).

(Continued)

*Primary Examiner* — Joseph Kosack
(74) *Attorney, Agent, or Firm* — Jenkins, Wilson, Taylor & Hunt, P.A.

(57) ABSTRACT

An isotope labeled asymmetric cross-linker is provided for the detection of cross-linked peptides. A cross-linking and mass spectrometry strategy, referred to as isotope tagging of interacting proteins (iTIP), improves the specificity of detecting cross-linked peptides and accurate identification of the interacting peptide sequences via the incorporation of isotopic signatures that are readily observed in the MS/MS spectrum. Isotope tagged peptides can be identified using mass spectrometry based on doublet peaks in a spectrum. Spectra can be subjected to database search strategies available for the sequencing of linear or non-cross-linked peptides.

4 Claims, 18 Drawing Sheets

(56) References Cited

OTHER PUBLICATIONS

King, G.J et al. Identification of disulfide-containing chemical cross-links in proteins using MALDI-TOF/TOF-mass spectrometry. Analytical chemistry 80, 5036-5043 (2008).
Lambert, W., Soderberg, C.A., Rutsdottir, G., Boelens, W.C. & Emanuelsson, C. Thiol-exchange in DTSSP crosslinked peptides is proportional to cysteine content and precisely controlled in cross-link detection by two-step LC-MALDI MSMS. Protein science: a publication of the Protein Society 20, 1682-1691 (2011).
Lambert, W. et al. Subunit arrangement in the dodecameric chloroplast small heat shock protein Hsp21. Protein science: a publication of the Protein Society 20, 291-301 (2011).
Li, H. & O'Connor, P.B. Electron capture dissociation of disulfide, sulfur-selenium, and diselenide bound peptides. Journal of the American Society for Mass Spectrometry 23, 2001-2010 (2012).
Lu, Y.; Tanasova, M.; Borhan, B.; Reid, G. E., Ionic reagent for controlling the gas-phase fragmentation reactions of cross-linked peptides. Anal Chem 2008, 80, (23), 9279-87.
Petrotchenko, E. V.; Xiao, K.; Cable, J.; Chen, Y.; Dokholyan, N. V.; Borchers, C. H., BiPS, a photocleavable, isotopically coded, fluorescent cross-linker for structural proteomics. Mol Cell Proteomics 2009, 8, (2), 273-86.
Petrotchenko, E. V.; Serpa, J. J.; Borchers, C. H., An isotopically coded CID-cleavable biotinylated cross-linker for structural proteomics. Mol Cell Proteomics 2011, 10, (2), M110 001420.
Petrotchenko, E. V.; Borchers, C. H., Crosslinking combined with mass spectrometry for structural proteomics. Mass Spectrom Rev 2010, 29, (6), 862-76.
Petrotchenko, E. V.; Borchers, C. H., ICC-CLASS: isotopically-coded cleavable crosslinking analysis software suite. BMC Bioinformatics 2010, 11, 64.
Petrotchenko, E. V.; Olkhovik, V. K.; Borchers, C. H., Isotopically coded cleavable cross-linker for studying protein-protein interaction and protein complexes. Mol Cell Proteomics 2005, 4, (8), 1167-79.
Petrotchenko, E. V.; Serpa, J. J.; Borchers, C. H. Use of a combination of isotopically coded cross-linkers and isotopically coded N-terminal modification reagents for selective identification of inter-peptide crosslinks. Anal Chem 2010, 82, (3), 817-23.
Ross, P.L. et al. Multiplexed protein quantitation in *Saccharomyces cerevisiae* using amine-reactive isobaric tagging reagents. Molecular & cellular proteomics :MCP 3, 1154-1169 (2004).
Schilling, B., Row, R.H., Gibson, B.W., Guo, X. & Young, M.M. MS2Assign, automated assignment and nomenclature of tandem mass spectra of chemically crosslinked peptides. Journal of the American Society for Mass Spectrometry 14, 834-850 (2003).
Sojo, L.E, Lum, G. & Chee, P. Internal standard signal suppression by co-eluting analyte in isotope dilution LC-ESI-MS. The Analyst 128, 51-54 (2003).
Swaim, C. L.; Smith, J. B.; Smith, D. L., Unexpected products from the reaction of the synthetic cross-linker 3,3'-dithiobis(sulfosuccinimidyl propionate), DTSSP with peptides. J Am Soc Mass Spectrom 2004, 15, (5), 736-49.
Syka, J. E.; Coon, J. J.; Schroeder, M. J.; Shabanowitz, J.; Hunt, D. F., Peptide and protein sequence analysis by electron transfer dissociation mass spectrometry. Proc Natl Acad Sci U S A 2004, 101, (26), 9528-33.
Tang, X.; Bruce, J. E., A new cross-linking strategy: protein interaction reporter (PIR) technology for protein-protein interaction studies. Mol Biosyst 2010, 6, (6), 939-47.
Thompson, A. et al. Tandem mass tags: a novel quantification strategy for comparative analysis of complex protein mixtures by MS/MS. Analytical chemistry 75, 1895-1904 (2003).
Walzthoeni, T. et al. False discovery rate estimation for cross-linked peptides identified by mass spectrometry. Nature methods 9, 901-903 (2012).
Weatherly, D. B.; Atwood, J. A., 3rd; Minning, T. A.; Cavola, C.; Tarleton, R. L.; Orlando, R., A Heuristic method for assigning a false-discovery rate for protein identifications from MASCOT database search results, Mol Cell Proteomics 2005, 4 (61), 762-72.
Xia, Y.; Cooks, R.G., Plasma induced oxidative cleavage of disulfide bonds in polypeptides during nanoelectrospray ionization. Anal Chem 2010, 82, (7), 2856-64.
Xie, H.; Braha, O.; Gu, L. Q.; Cheley, S.; Bayley, H., Single-molecule observation of the catalytic subunit of cAMP-dependent protein kinase binding to an inhibitor peptide. Chem Biol 2005, 12, (1), 109-20.
Zubarev, R.A. et al. Electron capture disassociation for structural characterization of multiply charged protein cations. Analytical chemistry 72, 563-573 (2000).

\* cited by examiner

PEAKS 2/3=LIGHT/HEAVY CROSS-LINKER PEPTIDE PAIR (1:1 DTSSP/D8-DTSSP)
PEAKS6/7=LIGHT/HEAVY CROSS-LINKER PEPTIDE PAIR (1:1 DTSSP/D8-DTSSP)
PEAK4=ISOBARIC CROSS-LINKER PEPTIDE (D4-DTSSP)
PEAKS 1,5=NON CROSS-LINKED PETIDES
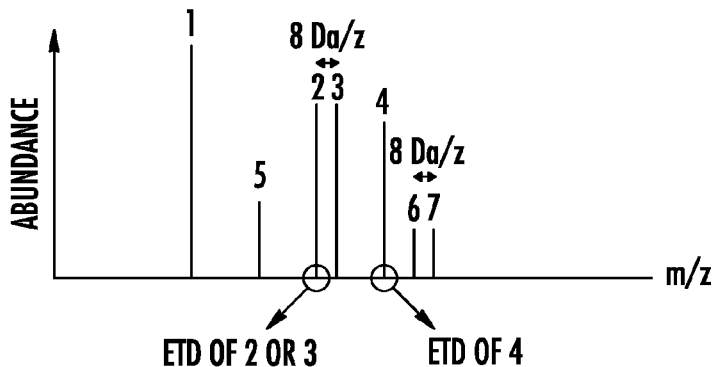
FIG. 4A
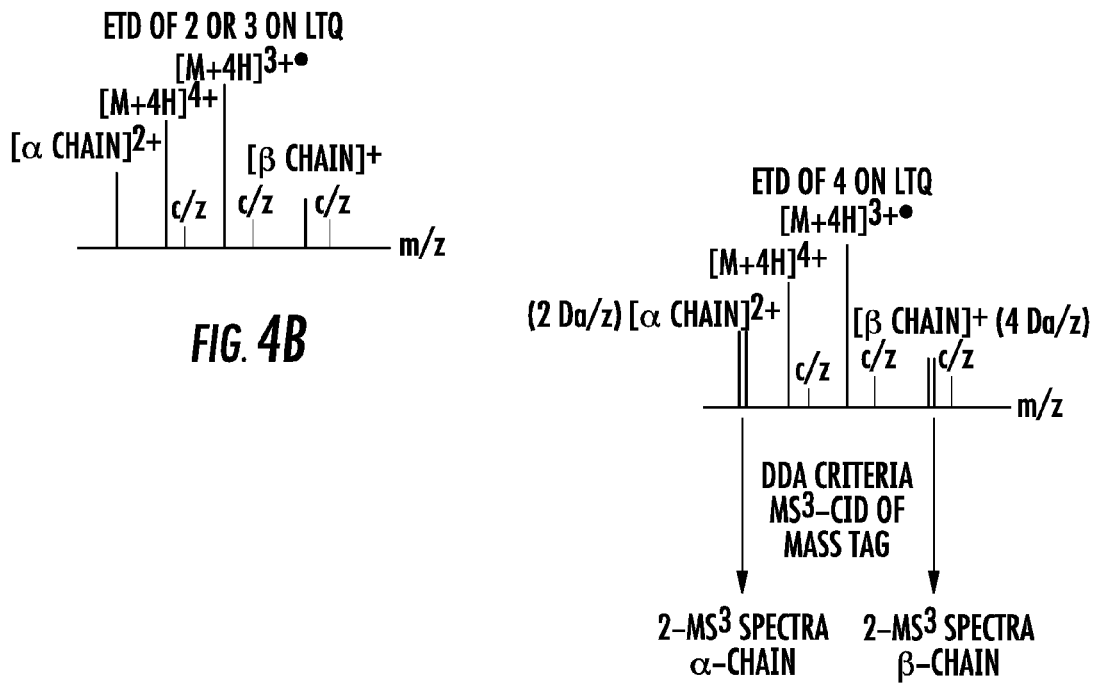
FIG. 4B
FIG. 4C
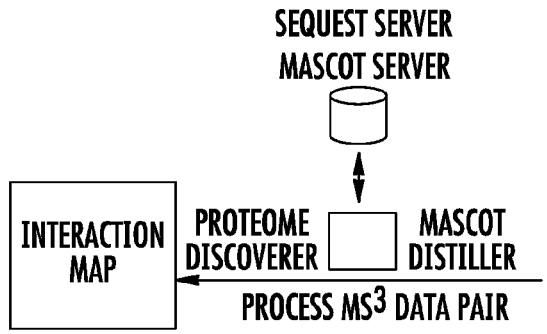
FIG. 4D

MASCOT CONFIGURATION: MODIFICATIONS

MODIFICATIONS

| ELEMENT | MONOISOTOPIC | AVERAGE | COPOSITION | HIDDEN |
|---|---|---|---|---|
| IMID | 68.037448 | 68.0773 | H(4) C(3) N(2) COPY PRINT | YES |
| IMID:2H(4) | 72.062555 | 72.1019 | 2H(4) C(3) N(2) COPY PRINT | YES |
| IMINOBIOTIN | 225.093583 | 225.3106 | H(15) C(10) N(3) O S COPY PRINT | YES |
| IODO | 125.896648 | 125.8965 | H(-1) I COPY PRINT | YES |
| IODOU-AMP | 322.020217 | 322.1654 | H(11) C(9) N(2) O(9) P COPY PRINT | YES |
| ISOPROPYLPHOSPHO | 122.013281 | 122.0596 | H(7) C(3) O(3) P COPY PRINT | YES |
| iTRAQ4PLEX | 144.102063 | 144.1544 | H(12) C(4) 13C(3) N 15N O COPY PRINT | NO |
| iTRAQ4PLEX114 | 144.105918 | 144.1680 | H(12) C(5) 13C(2) N(2) 18O COPY PRINT | YES |
| iTRAQ4PLEX115 | 144.099599 | 144.1688 | H(12) C(6) 13C N 15N 18O COPY PRINT | YES |
| iTRAQ8PLEX | 304.205360 | 304.3074 | H(24) C(7) 13C(7) N(3) 15N O(3) COPY PRINT | NO |
| iTRAQ8PLEX:13C(6)15N(2) | 304.199040 | 304.3081 | H(24) C(8) 13C(6) N(2) 15N(2) O(3) COPY PRINT | YES |
| K_NTERM_D4_S | 91.015567 | 91.1450 | 2H(4) C(3) H(-1) O S COPY PRINT | NO |
| K_NTERM_D4_SH | 92.023392 | 92.12529 | 2H(4) C(3) O S COPY PRINT | NO |
| K_NTERM_H4_S | 86.990460 | 87.1203 | C(3) H(3) O S COPY PRINT | NO |
| K_NTERM_H4_SH | 87.998285 | 88.1283 | C(3) H(4) O S COPY PRINT | NO |
| LABEL:13C(1)2H(3) | 4.022185 | 4.0111 | 13C 2H(3) C(-1) H(-3) COPY PRINT | NO |
| LABEL:13C(1)2H(3)+OXIDATION | 20.017100 | 20.0105 | 13C 2H(3) C(-1) H(-3) O COPY PRINT | NO |
| LABEL:13C(4)2H(2)+GLYGLY | 120.050417 | 120.0601 | H(6) 13C(4) 15N(2) O(2) COPY PRINT | YES |
| LABEL:13C(5) | 5.016774 | 4.9633 | C (-5) 13C(5) COPY PRINT | YES |
| LABEL:13C(5)15N(1) | 6.013809 | 5.9567 | C (-5) 13C(5) N(-1) 15N COPY PRINT | YES |

DYNAMIC MODIFICATIONS FOR iTIP (bracketing K_NTERM_D4_S through K_NTERM_H4_SH)

FIG. 5A

SEQUEST CONFIGURATION: MODIFICATION

| IS ACTIVE | MODIFICATION | ABBREVIATION | DELTA MASS | DELTA AVERAGE MASS | SUBSTITUTION | LEAVING GROUP | POSITION | UNIMOD ACCESSION NO. |
|---|---|---|---|---|---|---|---|---|
| ☐ | LYS->AMINOADIPICACID | LYS->AMINOADIPICACID | 14.96328 | 14.9683 | H(-3) N(-1) O(2) | | ANY | 38 |
| ☐ | LYS->ALLYSINE | LYS->ALLYSINE | -1.031634 | -1.0311 | H(-3) N(-1) O | | ANY | 35 |
| ☐ | LYS->ALA | LYS->ALA | -57.057849 | -57.0944 | H(-7) C(-3) N(-1) | | ANY | |
| ☑ | LYS_H4SH | LYS_H4SH | 87.998285 | 87.99 | H(4) C(3) S O | | ANY | 113 |

AMINO ACID NAME | ONE LETTER CODE | CLASSIFICATION
LYSINE | K | OTHER
*ADD A MODIFICATION...

| IS ACTIVE | MODIFICATION | ABBREVIATION | DELTA MASS | DELTA AVERAGE MASS | SUBSTITUTION | LEAVING GROUP | POSITION | UNIMOD ACCESSION NO. |
|---|---|---|---|---|---|---|---|---|
| ☑ | LYS_H4S | LYS_H4S | 86.99046 | 86.99 | H(3) C(3) S O | | ANY | |

AMINO ACID NAME | ONE LETTER CODE | CLASSIFICATION
LYSINE | K | OTHER
*ADD A MODIFICATION...

| IS ACTIVE | MODIFICATION | ABBREVIATION | DELTA MASS | DELTA AVERAGE MASS | SUBSTITUTION | LEAVING GROUP | POSITION | UNIMOD ACCESSION NO. |
|---|---|---|---|---|---|---|---|---|
| ☑ | LYS_H4S | LYS_H4S | 92.023392 | 92.02 | 2H(4) C(3) S O | | ANY | |

AMINO ACID NAME | ONE LETTER CODE | CLASSIFICATION
LYSINE | K | OTHER
*ADD A MODIFICATION...

| IS ACTIVE | MODIFICATION | ABBREVIATION | DELTA MASS | DELTA AVERAGE MASS | SUBSTITUTION | LEAVING GROUP | POSITION | UNIMOD ACCESSION NO. |
|---|---|---|---|---|---|---|---|---|
| ☑ | LYS_H4S | LYS_H4S | 91.015567 | 91.01 | 2H(4) H(-1) C(3) S O | | ANY | |

AMINO ACID NAME | ONE LETTER CODE | CLASSIFICATION
LYSINE | K | OTHER
*ADD A MODIFICATION...

| IS ACTIVE | MODIFICATION | ABBREVIATION | DELTA MASS | DELTA AVERAGE MASS | SUBSTITUTION | LEAVING GROUP | POSITION | UNIMOD ACCESSION NO. |
|---|---|---|---|---|---|---|---|---|
| ☐ | LIPOYL | LIPOYL | 188.032956 | 188.3103 | H(12) C(8) O S(2) | | ANY | 42 |
| ☐ | LG-PYRROLE | LG-PYRROLE | 316.203845 | 316.4345 | H(28) C(20) O S(3) | | ANY N T... | 942 |
| ☐ | LG-PYRROLE | LG-PYRROLE | 316.203845 | 316.4345 | H(28) C(20) O S(3) | | ANY | 942 |
| ☐ | LG-LACTAM-R | LG-LACTAM-R | 290.176961 | 290.3939 | H(26) C(19) N(-2) O(4) | | ANY | 508 |

FIG. 5B

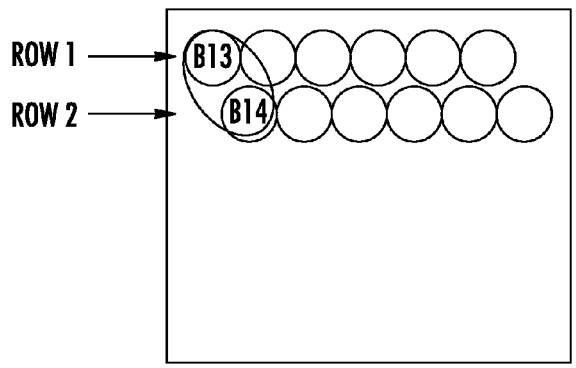
FIG. 13A
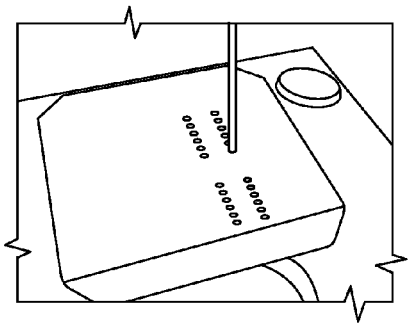
FIG. 13B
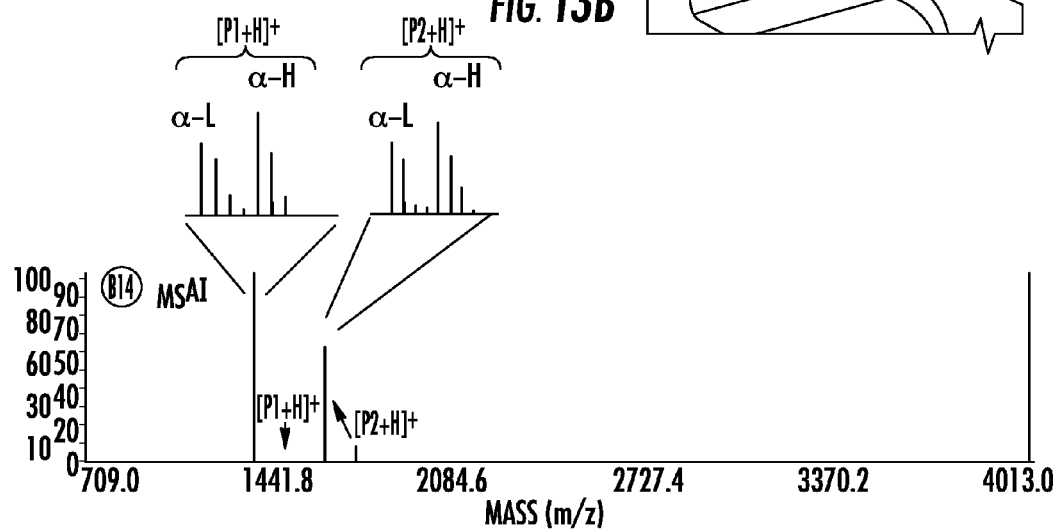
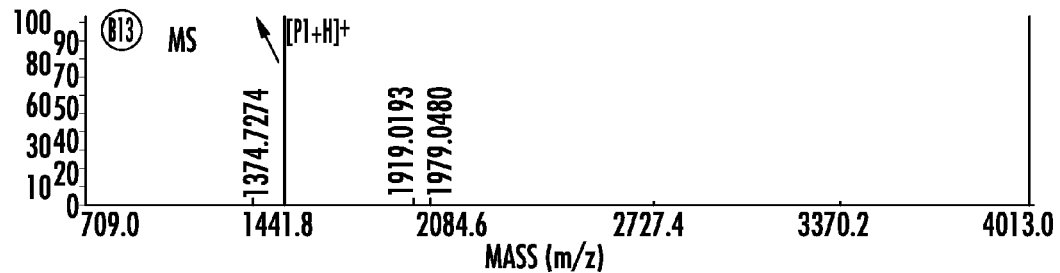
FIG. 13C

A.
MGLSDGEWQQ VLNVWGKVEA DIAGHGQEVL IRLFTGHPETLEKFDK FKHLK
TEAEMKASE DLKKHGTVVL TALGGILKKK GHHEAELKPL AQSHATK HKIPIK
YLEFISD AIIHVLHSKH PGDFGADAQG AMTKALELFR NDIAAKYKEL GFQG
(SEQ ID NO.1)
B. 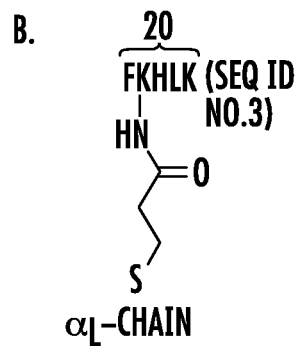
α_L-CHAIN
C. 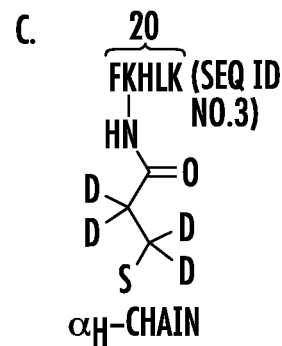
α_H-CHAIN
D. 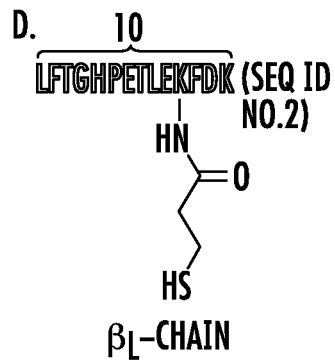
β_L-CHAIN
E. 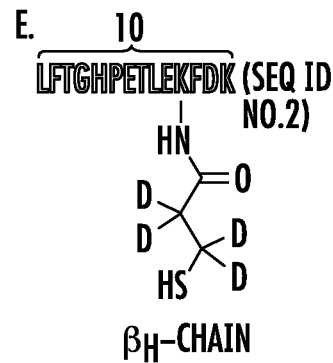
β_H-CHAIN
FIG. 15

| ACCESSION | COVERAGE | #PEPTIDES | #AAS | MW[kDa] | CALC.PI | SCORE | DESCRIPTION |
|---|---|---|---|---|---|---|---|
| P68082 | 46.10% | 334 | 154 | 17.1 | 7.81 | 14.74 | MYOGLOBIN-EQUUS (HORSE)-[MYG_HORSE] |

| | SEQUENCE | PROTEIN ACCESSIONS | #PROTEINS | #PROTEINS GROUPS | ACTIVATION TYPE | MODIFICATIONS | PROBABILITY | XCORR | ΔSCORE | ΔCN | RANK | CHARGE | M/Z[Da] | MH+[Da] | ΔM[PPM] | RT[MIN] | FIRST SCAN | LAST SCAN | MS ORDER |
|---|---|---|---|---|---|---|---|---|---|---|---|---|---|---|---|---|---|---|---|
| ○ | LFTGHPETLEKFDK | P68082 | 1 | 1 | CID,ETD | K11(LYS_D4SH) | 44.24 | 2.56 | 0.09 | | 1 | 2 | 877.20000 | 1753.39272 | -276.09 | 69.32 | 11922 | 11922 | MS3 |
| ○ | LFTGHPETLEKFDK | P68082 | 1 | 1 | CID,ETD | K11(LYS_D4SH) | 52.53 | 2.53 | 0.18 | | 1 | 2 | 875.20000 | 1749.39272 | -262.37 | 69.44 | 11945 | 11945 | MS3 |
| ▲ ○ | FKHLK | P68082 | 1 | 1 | CID,ETD | K2(LYS_D4SH) | 18.44 | 1.20 | 1.00 | | 1 | 1 | 763.33630 | 763.33630 | -128.97 | 69.97 | 12040 | 12040 | MS3 |
| ○ | FKHLK | P68082 | 1 | 1 | CID,ETD | K2(LYS_H4S) | 11.96 | 1.12 | 1.00 | | 1 | 1 | 759.65643 | 759.65643 | 324.87 | 70.08 | 12063 | 12063 | MS3 |

FIG. 16

CROSS-LINKING COMPOSITIONS AND RELATED METHODS OF ISOTOPE TAGGING OF INTERACTING PROTEINS AND ANALYSIS OF PROTEIN INTERACTIONS

CROSS REFERENCE TO RELATED APPLICATIONS

This application claims the benefit of U.S. Provisional Patent Application Ser. No. 61/755,282, filed Jan. 22, 2013, the disclosure of which is incorporated herein by reference in its entirety.

GRANT STATEMENT

This invention was made with government support under Grant No. AI064806 awarded by the National Institutes of Health. The government has certain rights in the invention.

TECHNICAL FIELD

The presently disclosed subject matter relates to cross-linking compositions for use in isotope tagging of interacting proteins. The presently disclosed subject matter also relates to methods of isotope tagging of interacting proteins and analysis of protein interactions using the disclosed cross-linking compositions.

BACKGROUND

Chemical-cross linking combined with proteolytic digestion and mass spectrometry is a promising approach to study protein-protein interactions. The distance constrains of the cross-linker between defined amino acid residues allows structural characterization of protein complexes. The gross three dimensional structure of a protein, contact interface between multi-protein complexes, stoichiometry and configuration of the constituent units of a complex are a few of the pieces of useful information that can be derived from cross-linking based mass spectrometry approaches. However, gas-phase dissociation reactions of protonated cross-linkers lack the sensitivity and specificity required to fragment the cross-linker at the desired location.

There remains a need, therefore, for improved cross-linkers for studying protein interactions. Methods of using improved cross-linkers in mass spectrometry for studying protein interactions are also needed.

SUMMARY

The presently disclosed subject matter provides isotope labeled amine reactive cross-linkers and a method of synthesizing isotope labeled amine reactive cross-linkers. The presently disclosed subject matter provides mass spectrometry processes and methods for characterizing protein interactions and protein-drug interactions.

An object of the presently disclosed subject matter having been stated hereinabove, and which is achieved in whole or in part by the presently disclosed subject matter, other objects will become evident as the description proceeds when taken in connection with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 4A to 4D are schematic illustrations of a cross-linking analysis workflow distinguishing stable isotope pairs in $MS^1$ and stable isotope pairs in $MS^2$;

FIGS. 5A and 5B are exemplary search engine configurations. FIG. 5A is a table of exemplary modifications for a MASCOT search engine, and FIG. 5B is an exemplary SEQUEST configuration editor;

FIG. 7A is a typical $MS^1$ spectrum when medium:light cross-linkers (1:1 mole ratio of DTSSP and asymmetric d4-DTSSP) are used, where the cross-linked peptides are observed in $MS^1$ (Full-MS high resolution accurate mass spectrum using FT-fourier transform Orbitrap mass analysis) as doublets peaks 1, 2 and peaks 3, 4 with a Δm of 4 Da/z. FIGS. 7B and 7C show spectra for peaks 1 and 2, respectively, after dissociation via $MS^2$-ET;

FIG. 8A shows the typical inter-linked peptides resulting in two constituent chains that differ in size. FIG. 8B shows a possibility of inter-linked peptides that are similar in size and perhaps similar in sequence. The peptides generated from multiple cross-links can in some embodiments be more complicated, as shown in FIGS. 8C and 8D;

FIG. 11A is a CID spectrum of m/z 1749.8=[β-L]⁺. FIG. 11B is a CID spectrum of m/z 685.4=[α-L];

FIGS. 13A to 13C illustrate the use of disclosed asymmetric cross-linkers in matrix-assisted laser desorption ionization (MALDI) mass spectrometry. FIG. 13A is a schematic illustrating a MALDI mass spectrometry method for electron-induced dissociation of d4-DTSSP using a MALDI spotting strategy. FIG. 13B is a graphic illustrating a MALDI plate spotted via an LC spotter. FIG. 13C is a full MS spectrum of intact peptides in Spot B13 and Full-MS spectrum of dissociated cross-linked peptides derived from Spot B14;

FIGS. 15A to 15E are schematic illustrations of cross-linker interactions with peptides in horse heart myoglobin after cleavage of the cross-linker disulfide bond;

FIG. 16 is an exemplary data output from a search engine used to identify proteins based on the ion spectra data.

DETAILED DESCRIPTION

Figure 1:
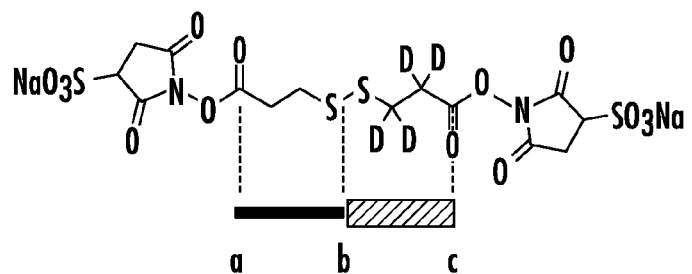
FIG. 1 is a schematic illustration of the chemical structure of the asymmetric cross-linker d4-DTSSP.

Provided herein are amine reactive cross-linkers that can in some embodiments be selectively fragmented at a specific location while rendering the dissociated cross-linked fragments to be distinguished from other backbone fragments. In some embodiments, provided herein are stable isotope labeled d4-DTSSP cross-linkers synthesized via asymmetric deuterium labeling of methylene carbon atoms located on one side of a S—S (disulfide) bond of a 3,3'-dithiobis (sulfosuccinimidyl sulfo propionate) molecule.

In some embodiments, a stable isotope labeled amine reactive cross-linker of the presently disclosed subject matter can comprise from about 4 to about 20 deuterium labels, in some embodiments from about 4 to about 8 deuterium labels. In some embodiments, the disulfide bond of a disclosed cross-linker can be dissociated or cleaved to form a heavy and light chain marker, wherein the heavy chain is that comprising the deuterium label or labels. In some embodiments, a cross-linker as disclosed herein can have a spacer length of about 12 Angstroms to about 27.4 Angstroms. Of this, the Sp3-Sp3 C—C bond length in a cross-linker can be about 1.54 Angstroms. This, coupled with the addition of one or more carbons, such as for example with the addition of 10 carbon atoms, to the existing DTSSP length results in the above length of the cross-linker.

In some embodiments, an amine reactive cross-linker as disclosed herein can attach to $NH_2$ of a lysine residue of a protein or peptide, or a N-terminus of a protein or peptide, during cross-linking between one or more interacting proteins, peptides or amino acids.

In some embodiments, methods of synthesizing isotope labeled amine reactive cross-linkers are disclosed. In some embodiments, a synthesis method can comprises combining into a mixture disulfide, tetrahydrofuran, water and 2,2',3, 3'-Tetradeuterium-3-mercaptopropanoic acid; stirring the mixture and concentrating the mixture under pressure; isolating the cross-linker by chromatography; mixing the isolated cross-linker with dimethylformamide, N-hydroxysulfosuccinimide sodium salt and dicyclohexylcarbodiimide; and isolating a cross-linker by centrifugation. In some embodiments, combining into a mixture disulfide, tetrahydrofuran, water and 2,2',3,3'-Tetradeuterium-3-mercaptopropanoic acid comprises mixing about 16.9 mg of disulfide, about 0.4 mL of tetrahydrofuran, about 0.3 mL of water, and about 83 uL of 2,2',3,3'-Tetradeuterium-3-mercaptopropanoic acid (1 M in $D_2O$).

In some embodiments, methods of employing a cross-linker in mass spectrometry for studying protein and/or peptide interactions, characterizing protein and/or peptide structure and/or identifying proteins and/or peptides, are provided. By way of example and not limitation, employing a stable isotope labeled d4-DTSSP cross-linker along with ETD-MS/MS, which can selectively fragment the S—S (disulfide) bonds, can provide for a unique asymmetric isotopic-tagging and detection strategy of cross-linked peptides. Due to the asymmetric nature of the cross-linker, doublets of reporter ions can be generated for each inter-linked peptide halves that differ in a mass by, for example 4 Da. The doublets of light and heavy-isotope labeled peptides can therefore be specific for only cleavage products associated with the cross-linker and hence diagnostic of each interacting protein and/or peptide pair.

In some embodiments, employing a disclosed cross-linker in mass spectrometry can also be used to cross-link a protein with a small molecule (e.g. a non-protein molecule), or two non-protein entities, wherein the structure for a cross-linker reaction is the presence of primary amines or $NH_2$ groups.

In some embodiments, the product ions resulting from cross-linker cleavage can be distinguished from other ETD product ions such as peptide backbone products, side-chain losses, and charge reduced species. The unique selectivity advantage of distinguishing diagnostic reporter ions can markedly improve the ability of this technique to identify inter-linked proteins and/or peptides as compared to previous methods that require sensitive detection of the cross-linked cleavage products. Each of the peptides cleaved at the S—S bond can be structurally interrogated via CID-MS/MS. In some aspects, the MS³-CID product ion spectra of each peptide half can form the basis for their identification and hence the identification of an interacting protein/peptide. The disclosed cross-linking strategy by which specific interacting proteins/peptides are identified can in some embodiments be referred to as isotope tagging of interacting proteins (iTIP).

In some embodiments, the mass spectrometry of the iTIP methods can utilize electron spray ionization (ESI) or matrix-assisted laser desorption ionization (MALDI). In some embodiments, an MS³ step can employ CID or High Energy Collision Dissociation (HCD).

In some embodiments, mass spectrometry methods of the presently disclosed subject matter which employ the disclosed stable isotope labeled d4-DTSSP cross-linker can increase the sensitivity of identifying proteins and/or peptides since CID data from both heavy and light pair-wise peptide identifications can be rolled-up to the protein-level that results in an increased confidence in the assignment of peptides to proteins as a result of doubling the number of peptides (data points) used to identify a protein by either searching a database or spectral library.

In some embodiments, the presently disclosed iTIP methods can comprise the use of a disclosed stable isotope labeled d4-DTSSP cross-linker in conjunction with a crosslinker that is not asymmetrically deuterated, to increase the sensitivity of identifying proteins.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

Turning now to the Figures, FIG. 1 is a schematic illustration of the chemical structure of an exemplary isotope labeled amine reactive asymmetric cross-linker, and particularly an asymmetric cross-linker d4-DTSSP. Asymmetric d4-DTSSP comprises amine reactive sites a, c and cleavable site b. In some aspects cleavable site b is cleavable by ETD, for example. Asymmetric d4-DTSSP, as illustrated in FIG. 1, and as fully characterized by NMR comprises $^1$H NMR (CDCl$_3$, 400 MHz), δ 3.11-3.15 (m, 2H), 3.19-3.26 (m, 4H), 3.40 (d, J=9.2 Hz, 1H), 3.44 (d, J=9.6 Hz, 1H), 4.33 (d, J=8.8 Hz, 1H), 4.52 (d, J=8.8 Hz, 1H).

In some aspects, an isotope labeled amine reactive cross-linker is provided, wherein the cross-linker comprises a 3,3'-dithiobis(sulfosuccinimidyl sulfo propionate) molecule comprising a disulfide bond, and a deuterium label positioned on one side of the disulfide bond of the 3,3'-dithiobis (sulfosuccinimidyl sulfo propionate) molecule, wherein the deuterium label causes the 3,3'-dithiobis(sulfosuccinimidyl sulfo propionate) molecule to be structurally asymmetrical across the disulfide bond. In some embodiments, the deuterium label is on a methylene carbon of the 3,3'-dithiobis (sulfosuccinimidyl sulfo propionate) molecule. In some embodiments, the deuterium label comprises 1, 2, 3, 4, 5, 6 or 7 deuterium labels. As discussed herein, the deuterium label can cause mass asymmetry in the 3,3'-dithiobis (sulfosuccinimidyl sulfo propionate) molecule.

In some aspects, the disulfide bond of the cross-linker can be dissociated, such as for example using electron transfer dissociation (ETD), Negative ion collision induced dissociation, high energy collision induced dissociation (HCD), low temperature plasma ionization (LTPI) of ESI generated ions, MALDI with a matrix that dissociates S—S bonds, and reactive desorption electrospray ionization (Reactive DESI). In some embodiments, dissociation of the disulfide bond creates a first and a second cleavage product, wherein one of the first or second cleavage products comprises the deuterium label, wherein the first and a second cleavage products differ in mass. In some embodiments, the nominal mass of a cleavage products differs by 4 Daltons.

In some embodiments, an amine reactive cross-linker as disclosed herein can bind at both carbonyl carbons with a NH$_2$ group of a lysine residue or N-terminus within a single protein. In some embodiments, the amine reactive cross-linker can bind at both carbonyl carbons with a NH$_2$ group of a lysine residue or N-terminus of separate interacting proteins of a complex. In some aspects, the cross-linker can have a length of about 12 Angstroms to about 27.4 Angstroms.

As discussed further herein, in some aspects the cross-linker can be extended by up to 10 additional carbons. Additionally, in some embodiments, the deuterium label can comprise 1, 2, 3, 4, 5, 6, 7, 8, 9, 10, 11, 12, 13, 14, 15, 16, 17, 18, 19 or 20 deuterium labels.

By way of example and not limitation, an asymmetric cross-linker can in some embodiments comprise a d4-DTSSP with 4 deuterium atoms incorporated on two methylene carbons located on one side of the disulfide bond giving a Δm of 4 Da, when the cross-linker is cleaved by ETD at position b while attached to two amine residues of the peptide(s) at positions a and c (see FIG. 1). The stable isotopes are incorporated in DTSSP via asymmetric positioning of four deuterium labels on two of the four methylene carbons, giving rise to a mass asymmetry across the two-fold axis of the S—S bond. Except for the asymmetric positioning of four deuterium labels, d4-DTSSP is structurally analogous to DTSSP. The bidirectional orientation of the cross-linker facilitates two fragments in the ETD spectrum for each constituent chain by tagging of heavy c-b segments or light a-b segments (see FIG. 1) of the cross-linker to an amine group of a N-terminus or lysine residue of a protein and/or peptide via acylation chemistry and the subsequent ETD cleavage of cross-linker at position b of the S—S bond.

To elaborate, the unique asymmetric isotope tagging signature of the disclosed cross-linkers can be detected via the selective electrons-transfer dissociation of the disulfide bond of the cross-linker. The asymmetric nature of the cross-linker can render a doublet of reporter ions with a mass off-set of 4 Da per unit charge for each inter-linked peptide halves due the equal likelihood orienting the light and heavy ends of the cross-linker during the reaction. The h4 (four hydrogen atoms) and d4 (four deuterium atoms) doublets (light and heavy-isotope tags attached to the constituent peptides) are therefore specific for only cleavage products associated with the disulfide cross-linker and hence diagnostic of each interacting peptide pair. The small mass off-set makes these fragment ions predictable, easy to visualize, and easily distinguishable from other ETD product ions such as peptide backbone products, side-chain losses, and charge reduced species which are single peaks. Each of the peptides cleaved at the S—S bond can be structurally interrogated via $MS^3$-CID where the product ion spectra of each peptide half can form the basis for their identification and hence the identification of an interacting protein, also referred to as iTIP.

The disulfide bond of the presently disclosed asymmetric d4-DTSSP (inter-linked to peptides), or any other asymmetric cross-linker disclosed herein, can be subjected to a number of electron or radical mediated dissociation techniques. By way of example and not limitation, electron capture (ECD), 257 nm UV photo dissociation, and/or low temperature plasma of electrospray (ESI) generated ions are few alternative techniques to the electron transfer dissociation (ETD) method for ESI generated cross-linked peptide cations. Additionally, in some embodiments disulfide-linked peptides can be efficiently dissociated at the S—S (disulfide) bond via negative ion collision induced dissociation (neg-CID) and gas-phase ion/ion reactions between gold anions $[Au(I)Cl_2]^-$.

Asymmetric cross-linkers, as illustrated in FIG. 1, can in some embodiments be extended to any desired length, using for example, starting materials selected from the group consisting of 6-mercaptohexanoic acid, 8-mercaptooctonoic acid, and/or 4-mercaptobutyric acid. Synthesis (see FIG. 2 as discussed hereinbelow) of asymmetric linkers as disclosed herein of different linker lengths can in some embodiments enable the determination of distances or interaction space between or within a protein.

In the disclosed asymmetric cross-linkers, the disulfide bond cleavage is quite facile in electron induced dissociation methods such as ECD and ETD of disulfide-linked polypeptides. The ETD spectra in particular gives product ions of the constituent polypeptides resulting from disulfide bond dissociation as the major product ions. Thus, the disclosed cross-linkers can provide for facile disulfide bond cleavage products of inter-linked polypeptides, proteins and/or peptides of cross-linker containing disulfide functionality.

Disulfide containing cross-linkers such as 3,3'-dithiobis (sulfosuccinimidyl sulfo propionate) (DTSSP) and 3,3'-dithiobis(sulfosuccinimidyl propionate) (DSP) and their isotopic derivatives all have a two-fold symmetry across the disulfide bond. These disulfide cross-linkers and other cross-linkers that have stable isotope counterparts allow for distinguishing cross-linked products selectively in a full MS or $MS^1$ scan when used as a 1:1 mole ratio, for example, of light and heavy stable isotope variants of cross-linker. Although such an isotope labeling strategy can improve the selectivity of detecting cross-linkers in $MS^1$, the overall sensitivity is decreased for every detectable cross-linked or dead-end peptide due to ion suppression effects during electrospray ionization. In addition, the use of stable isotope tags for the detection of cross-linked peptide precursors can challenging due to matrix interferences, low signal/noise issues inherent to a full MS spectrum and retention time-shifts in reversed-phase chromatography between the deuterated/O18 labeled peptides and their protonated counterparts. The number of labeled peptide can also impact the duty cycle of the instrument in data dependent acquisition (DDA) methods that usually pick the top 10-20 most abundant ions for MS/MS.

In order to circumvent these issues, the disclosed cross-linkers are provided with structural features amenable for their detection in $MS^2$ or MS/MS spectra with a high degree of specificity and improved signal-to-noise. Previous disulfide containing cross-linkers are structurally symmetrical across the disulfide bond, with a two-fold symmetry, allowing each constituent chain to result in identical mass-tags in the ETD-$MS^2$ spectra. The cross-linker design strategy disclosed herein is based on a mass off-set or ($\Delta m$) around the S—S bond. The bidirectional orientation of the cross-linker facilitates two fragments for each constituent chain with a mass off-set corresponding to the mass off-set across the disulfide bond. As disclosed herein, a mass difference can be analytically useful as it can serve at least two purposes. For example, the specificity can permit cross-linked products to be readily distinguished from other cleavages due to the fact that dissociation results in two distinct fragment ions with a specific mass off-set for each constituent chain (doublet of peaks) in the $MS^2$ spectrum. Additionally, both variants of a given peptide chain can in some embodiments be structurally interrogated via CID-$MS^3$ providing an additional degree of confidence in their sequence determination and identification.

The asymmetry across the disulfide bond can be rendered in a multitude of ways. However, an objective of the asymmetric cross-linking designs disclosed herein is to provide a mass off-set with minimum perturbation to the overall length and stereochemistry of the cross-linking molecules. By way of example and not limitation, an asymmetric cross-linker can in some embodiments comprise a d4-DTSSP with 4 deuterium atoms incorporated on two methylene carbons located on one side of the disulfide bond giving a $\Delta m$ of 4 Da, when the cross-linker is cleaved by ETD at position b while attached to two amine residues of the peptide(s) at positions a and c, as illustrated in FIG. 1.

For d4-DTSSP, the reporters derived from the cross-linker dissociation at the disulfide bond results in a 4 Da/z doublet of reporter ions. The reporter ions generated by the disclosed cross-linkers are not distinct masses rather they are observed as a doublet with a distinct $\Delta M$ (mass-off set). For example, the most commonly observed singly charged cross-linker containing product ions have a 4 Da nominal mass difference, while a doubly charged cross-linker product ion can in some embodiments have a 2 Da nominal mass difference in the doublet peaks. The m/z separation can be easily distinguishable from ETD spectra with a high degree of specificity. The initial diagnosis of the cross-linked pairs via features detection of gas-phase generated isotopic tags reduces the complexity of the data analysis. The identification of interacting proteins within the distance constraints of the cross-linker can be carried out by $MS^3$-CID of each constituent chain that results in sequence ions of each constituent linear peptide that are easily interpreted via protein sequence databases and search algorithms. As discussed herein, this strategy of identifying and localizing the sites of non-covalent interactions of proteins can be referred to as Isotope Tagging of Interacting Proteins (iTIP).

Figure 3A:
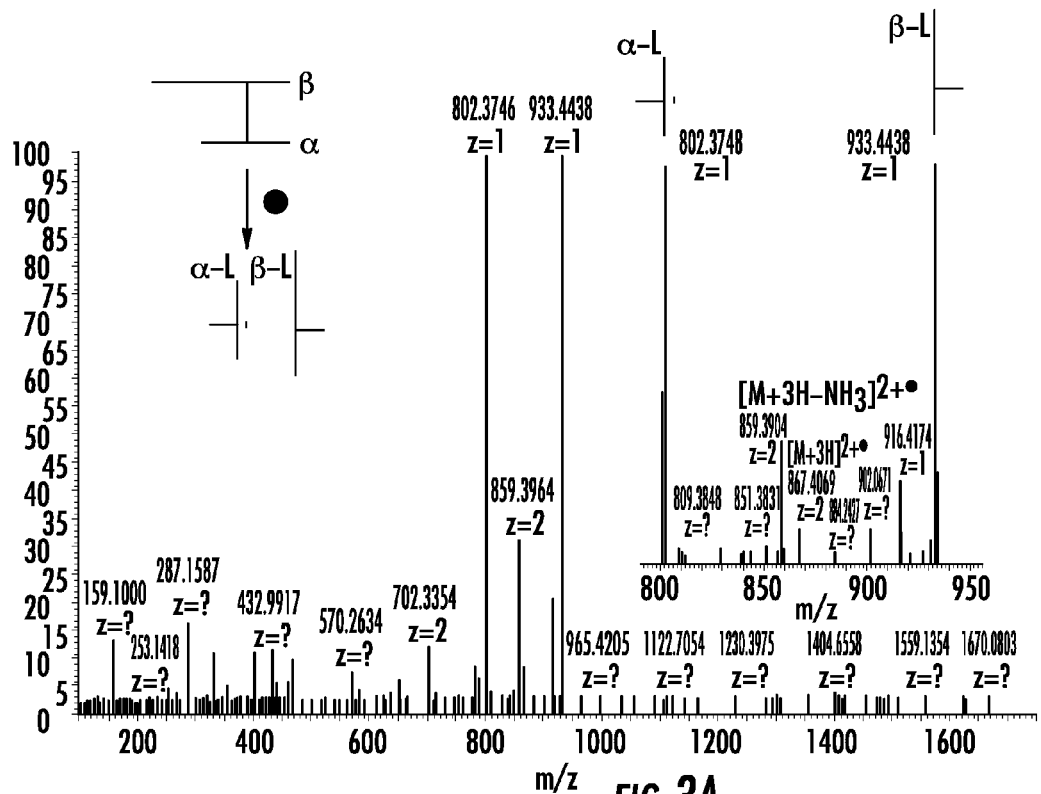
FIGS. 3A and 3B are MS spectrum illustrating the spectral differences visible when using a DTSSP cross-linker (FIG. 3A) as compared to an asymmetric d4-DTSSP cross-linker as disclosed herein (FIG. 3B)
Figure 3B:
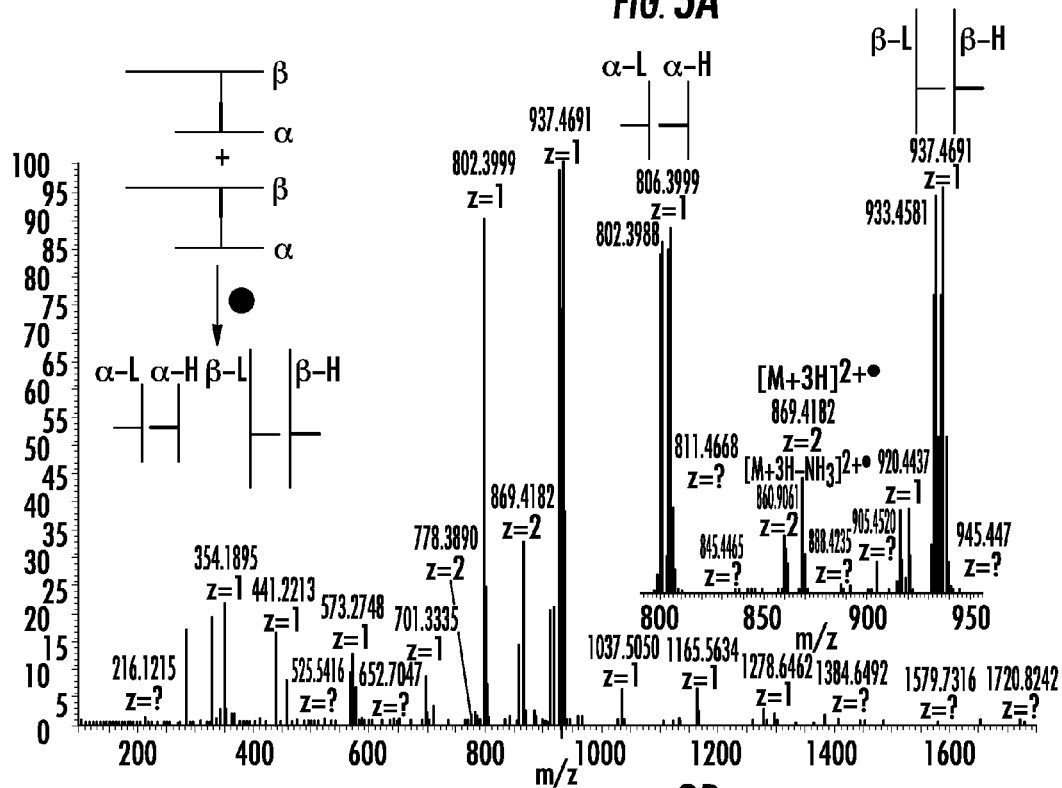

By way of illustration, and as discussed further herein, FIGS. 3A and 3B are MS spectrum illustrating the spectral differences visible when using a DTSSP cross-linker (FIG. 3A) as compared to an asymmetric d4-DTSSP cross-linker as disclosed herein (FIG. 3B). FIG. 3A is an ETD-MS/MS spectrum of inter-linked peptide between the reaction of ubiquitin and DTSSP. The inset shows dissociation of the cross-linker to yield the constituent α and β peptides. FIG. 3B is an ETD-MS/MS spectrum of the same polypeptide pairs inter-linked via asymmetric d4-DTSSP. The inset shows dissociation of the cross-linker to yield the constituent α-L and α-H polypeptide and β-L and β-H polypeptide.

FIG. 3A shows the ETD product ion spectrum of inter-linked polypeptide resulting from a cross-linking reaction of Ubiquitin and DTSSP (asymmetrical cross-linker). The product ions consist of mainly α and β chains that are single isotope clusters resulting from the direct cleavage of the DTSSP disulfide bond. FIG. 3B shows the ETD product ion spectrum of the same constituent polypeptide chains inter-linked with an asymmetric d4-DTSSP as disclosed herein. The product ion spectrum looks quite similar to FIG. 3A. However, due to the asymmetry on either sides of the S—S bond, and due to the bidirectional orientation of cross-linkers during the cross-linker reaction step, a doublet of peaks was observed for both α and β chains that are labeled as α-L/α-H and β-L and β-H. Such cross-linkers with asymmetric labeling can be analytically useful as they encode isotopic tags of cross-linked product ions to be readily distinguished from other cleavages due to dissociation of the cross-linker resulting in two distinct fragment ions for each constituent peptide chain and contain a specific mass signature that is observed as a doublet of peaks in the $MS^2$ spectrum.

Figure 2:
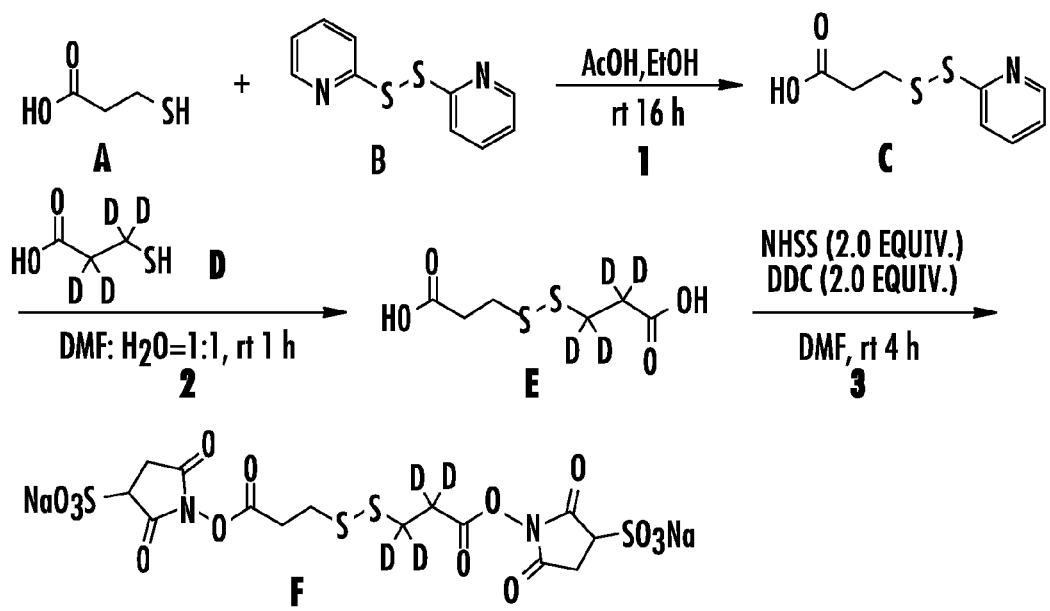
FIG. 2 is a schematic illustration of the synthesis of an isotope labeled amine reactive cross-linker, and particularly the asymmetric cross-linker d4-DTSSP.

Asymmetric d4-DTSSP and other asymmetric linkers can in some embodiments be synthesized as illustrated in FIG. 2 and as disclosed herein. A disulfide, tetrahydrofuran, water and 2,2',3,3'-Tetradeuterium-3-mercaptopropanoic acid can be mixed together in some embodiments. The resultant compound in dimethylformamide (DMF) can be mixed with N-hydroxysulfosuccinimide (NHSS) sodium salt and dicyclohexylcarbodimide (DDC). A cross linker can then be obtained after a series of centrifugations. Thus, a method of synthesizing an isotope labeled amine reactive cross-linker can in some aspects comprise combining into a mixture disulfide, tetrahydrofuran, water and 2,2',3,3'-Tetradeuterium-3-mercaptopropanoic acid, stirring the mixture and concentrating the mixture under pressure, isolating the cross-linker by chromatography, mixing the isolated cross-linker with dimethylformamide, N-hydroxysulfosuccinimide sodium salt and dicyclohexylcarbodimide, and isolating the cross-linker by centrifugation.

In some aspects, referring to FIG. 2, 3-mercaptopropanoic acid ($C_3H_6O_2S$; MW 106.14) A and 1,2-di(pyridine-2-yl)disulfane ($C_{10}H_8N_2S_2$; MW 220.31) B can be mixed with an acid (such as AcOH) and an alcohol (such as EtOH) at room temperature in step 1 to yield 3-(pyridine-2-yldisulfanyl)propanoic acid ($C_8H_9NO_2S_2$; MW 215.29) C. The mixing can in some embodiments take place for about 16 hours (hr). In step 2, 3-(pyridine-2-yldisulfanyl)propanoic acid C can be mixed with 2,2',3,3'-Tetradeuterium-3-mercaptopropanoic acid D in DMF and $H_2O$ (1:1) at room temperature to yield 3-((2-carboxyethyl)disulfanyl)propanoic-2,2,3,3-$d_4$ acid E. The mixing can in some embodiments take place for about 1 hr. In step 3, 3-((2-carboxyethyl)disulfanyl)propanoic-2,2,3,3-$d_4$ acid E can be mixed in DMF with NHSS and DCC at room temperature to yield sodium 1-((3-((3-((2,5-dioxo-3-sulfonatopyrrolidin-1-yl)oxy)-3-oxopropyl)disufanyl)propanoyl-2,2,3,3-$d_4$)oxy)-2,5-dioxopyrrolidine-3-sulfonate F (also referred to as d4-DTSSP). The mixing in step 3 can be at room temperature for about 4 hours.

In some embodiments, the disulfide, tetrahydrofuran, water and 2,2',3,3'-Tetradeuterium-3-mercaptopropanoic acid are combined successively at room temperature (rt). Moreover, in some aspects, combining into a mixture disulfide, tetrahydrofuran, water and 2,2',3,3'-Tetradeuterium-3-mercaptopropanoic acid can comprise mixing about 16.9 mg of disulfide, about 0.4 mL of tetrahydrofuran, about 0.3 mL of water, and about 83 uL of 2,2',3,3'-Tetradeuterium-3-mercaptopropanoic acid (1 M in $D_2O$). The chromatography can in some aspects be flash chromatography using silica gel and $CH_2Cl_2$:MeOH=95:5 with 0.4% formic acid. In some aspects, mixing the isolated cross-linker with dimethylformamide, N-hydroxysulfosuccinimide sodium salt and dicyclohexylcarbodimide comprises mixing with a solution of the isolated cross-linker (4.3 mg, 20 umol) about 0.3 mL dimethylformamide, about 8.7 mg N-hydroxysulfosuccinimide sodium salt and about 8.3 mg dicyclohexylcarbodimide. Furthermore, in some embodiments a method of synthesizing an isotope labeled amine reactive cross-linker can comprise drying a cross-linker precipitate obtained from the centrifugation, wherein the dried cross-linker precipitate forms a solid material.

Still yet, in other embodiments, the presently disclosed subject matter can comprise a scaled-up method of synthesizing a disclosed cross-linker, wherein the ranges given above can vary by as much as about 25%. In some aspects, as would be appreciated by one of ordinary skill in the art, the ranges of compounds and chemicals described above in a method of synthesizing a disclosed cross-linker, and illustrated in FIG. 2, can vary by as much as about 5%, 10%, 15%, 20%, 25%, or more, without departing from the scope of the instant disclosure. Likewise, as one of ordinary skill in the art will appreciate, the starting materials, temperatures, solvents and corresponding industrial processes can be optimized without departing from the scope of the instant disclosure.

In some embodiments, a method of synthesizing d4-DTSSP, as illustrated in FIG. 2, can be scaled-up by taking into consideration one or more factors in one or more of the steps. For example, in step 1 (FIG. 2), the sulfide, solvent(s), temperature and/or scale-up volume can be adjusted without departing from the scope of the instant disclosure. In particular, the sulfide (compound B in FIG. 2) can have chemical groups on one or both sides of the disulfide (S—S) bond that are aromatic and/or alkyl. The solvent can comprise a mix of acid and alcohol, or be 100% acid, wherein the alcohol can be selected from the group consisting of: EtOH, MeOH and IPA, and the acid can be selected from the group consisting of AcOH and TFA. Continuing with step 1, the temperature can range from 0° C. to reflux. Finally, in step 1 up to 10 times the volume of solvent to substrate can be used, with external controls of temperature used in some embodiments to avoid any possible exotherms.

Step 2 of FIG. 2 can be scaled-up and/or optimized as well without departing from the scope of the instant disclosure. For example, the sulfide, solvent(s), temperature and/or scale-up volume can be adjusted. In particular, the sulfide (compound C in FIG. 2) can have chemical groups on one or both sides of the disulfide (S—S) bond that are aromatic and/or alkyl (usually to a lesser extent). The solvent can comprise polar solvents (THF, DMF, NMP and/or DMSO) with water. Continuing with step 2, the temperature can range from 0° C. to reflux. Finally, in step 2, even though some experimental procedures herein use about 41 volumes of solvent to substrate, in scale up situations less volume can be used with external controls of temperature to avoid any possible exotherms.

Finally, in step 3 of FIG. 2, the parameters can be scaled-up and/or optimized as well without departing from the scope of the instant disclosure. For example, the solvent(s), temperature, protection group and/or scale-up volume can be adjusted. In particular, the solvent can comprise polar solvents selected from the group comprising THF, DMF, NMP, DMSO and/or DCM. Continuing with step 3, the temperature can range from 0° C. to reflux. The protecting group could be any type of succinimide with any carbodiimide, and in some embodiment any protecting group with any protecting condition. Finally, in step 3, even though some experimental procedures herein use about 70 volumes of solvent to substrate, in scale up situations less volume can be used with external controls of temperature to avoid any possible exotherms.

In some embodiments, the iTIP procedure can start with cross-linking of whole protein molecules, peptide, or complexes thereof with asymmetric d4-DTSSP, or other asymmetric cross-linkers as disclosed herein. An asymmetric cross-linker can be incorporated by acylation chemistry to bridge two primary amines within a single protein or peptide, between two proteins or peptides at positions a, c of d4-DTSSP (see FIG. 1), or to form a tethered attachment consisting of a single free-end of the entire cross-linker or it's hydrolyzed product. These reaction outcomes can give rise to intramolecular, intermolecular, or dead-end cross-linked proteins, respectively. In some embodiments, the proteins can then be proteolytically digested to inter-peptide cross-links that serve as structural surrogates for determining protein-protein interactions or peptide-peptide interactions. Depending on the sample complexity, tryptic peptide mixtures can be directly subjected to LC-MS/MS or fractionated off-line by strong cation exchange (SCX) chromatography and each fraction subjected to LC-MS/MS.

An exemplary LC-MS work flow is shown in FIGS. 4A-4D where inter-peptide cross-linked products are identified via data dependent ETD-MS/MS. FIGS. 4A to 4D illustrate a cross-linking analysis workflow distinguishing stable isotope pairs in $MS^1$ and stable isotope pairs in $MS^2$ observed in iTIP. FIG. 4A is a typical $MS^1$ spectrum when heavy:light cross-linkers are used in a 1:1 mole ratio, peptides are observed in $MS^1$ spectrum (Full-MS high resolution accurate mass spectrum using FT-fourier transform Orbitrap mass analysis) as doublets peaks 2, 3 and peaks 6, 7. FIG. 4B includes spectrum illustrating that for iTIP the cross-linker has a constant isobaric mass in $MS^1$ (Peak 4) and the isotopes differences are encoded in the peptide halves after dissociation via $MS^2$-ETD. Each peptide half is a doublet of α-chain and doublet of β-chain as seen in the right spectrum of FIG. 4B. When a cleavable-cross-linker that is not asymmetric, e.g. DTSSP, is used no doublet is produced as the cross-linker itself is symmetric across the cleavable site as seen in the left spectrum of FIG. 4B. FIG. 4C is a schematic illustrating that each chain is subjected to $MS^3$-CID and the spectra are processed via a search engine such as MASCOT. FIG. 4D is a schematic illustrating that identifications are mapped to a pair of interactions.

As illustrated in FIG. 4A, the top 5 most intense precursor ions can be mass selected and first subjected to ETD (FIGS. 4B and 4C). The diagnostic fragments due to the dissociation of cross-linked products can be identified in the ETD spectra seen as doublets (FIG. 4C). These doublets peaks can then be structurally interrogated via a second step of $MS^3$-CID (FIG. 4C) resulting in sequence ions for the doublet α-chain$_{Light}$, α-chain$_{Heavy}$, and doublet β-chain$_{Light}$, β-chain$_{Heavy}$ that are the constituent peptide chains of the interacting pairs of proteins. Each type of chain is distinguishable by their respective isotope spacing encoded in Light-H4 methylene carbons and Heavy-D4 methylene carbons of the cross-linker. The sequence ion spectra can then be filtered using scan-filtering procedures and can be searched against a protein sequence data base to identify the peptide (FIG. 4D), and localize the cross-linked label within each peptide, which were defined in the search engine configuration for modifications. By way of example and not limitation, a configuration of modification is presented FIG. 5A.

In FIG. 5A, the chemical compositions and masses of the dynamic modifications listed in the configuration table are the disulfide cleavage products of the d4-DTSSP crosslinker. The four possible modification masses are specified for N-terminus or lysine residues which are the locations of the cross-linker reactivity. The possible modification list can be reconfigured for any cross-linker compositions, including for example the cross-linkers that are of varying lengths. The configuration table for modifications (FIG. 5A) is an example for a MASCOT search engine. However, modification mass and specificities can be implemented with any available search engine, including for example the SEQUEST search engine. An exemplary SEQUEST configuration editor with cross-linker modifications, D4-SH, D4S, H4SH, H4S is illustrated in FIG. 5B.

Figure 6:
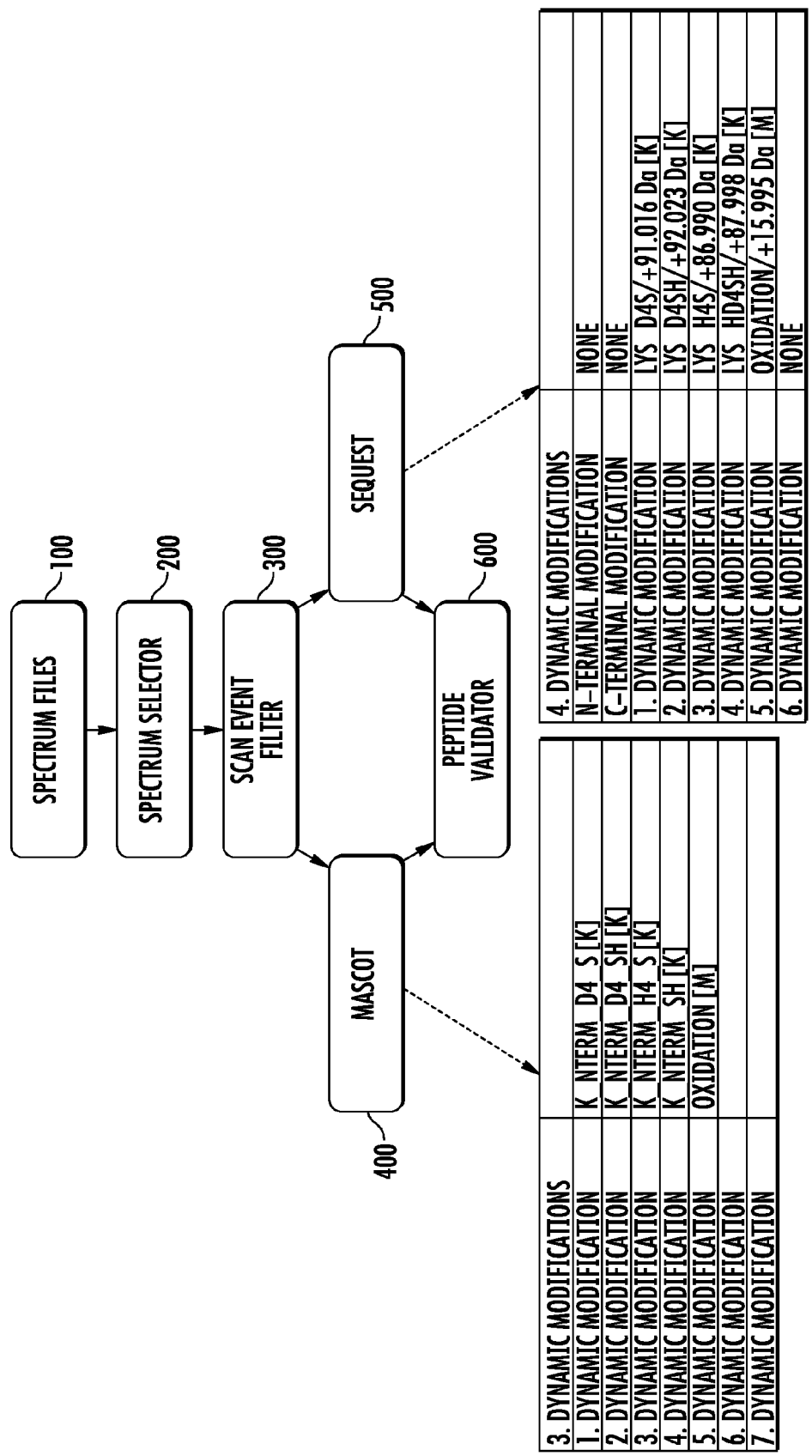
FIG. 6 is a schematic of an exemplary work flow illustrating the filtration and search of ion spectra data using both SEQUEST and MASCOT search engines.

An exemplary search workflow illustrating the filtration and search of ion spectra data using one or both SEQUEST and MASCOT search engines is illustrated in FIG. 6. Spectrum files 100 can in some embodiments be selected using spectrum selector 200. $MS^3$ spectra can be filtered using scan event filter 300 (or related scan-filtering procedures), which are only the CID spectra of the associated cross-lined peptide pairs. Subsequent searches can be performed using a search engine, such as for example MASCOT 400 or SEQUEST 500, and compared against a protein sequence data base to identify the peptide. In some embodiments, identified proteins can be validated using peptide validator 600.

The constituent peptide halves when extrapolated to the $MS^2$-ETD spectrum can result in the identification of each interacting protein or each interacting lysine residue within a protein. The LC-MS work flow shown in FIGS. 4A-4D illustrates the use of a 1:1 mixture of cross-linkers H8-DTSSP and DTSSP where doublets are detected only in MS$^1$ and compares the resulting spectra with the asymmetric d4-DTSSP used in the iTIP strategy where doublets are detected only in MS$^2$.

In some embodiment, another level of specificity can be added to the iTIP workflow if d4-DTSSP is used in conjunction with a non-deuterated and symmetric cross-linker, such as for example D8-DTSSP or DTSSP. Peptides cross-linked with a 1:1 mixture of asymmetric d4-DTSSP and D8-DTSSP (or DTSSP) can be seen as doublet in MS$^1$ with peak spacing of 4 Da per charge-unit (4 Da/z). Although not intending to be limited by any particular theory of operation, it is believed that the rationale for this extended strategy is to have additional specificity required to selectively perform ETD-MS/MS based on the observation of cross-linked peptide doublets in the full-MS or MS$^1$. (The Data dependent acquisition (DDA) methods in current mass spectrometers could recognize pairs of peaks in the peak picking criteria). In some embodiments, such a strategy can afford an addition level of specificity towards identifying d4-DTSSP containing cross-linked peptides. See, for Example FIGS. 7A-7C.

Figure 7A:
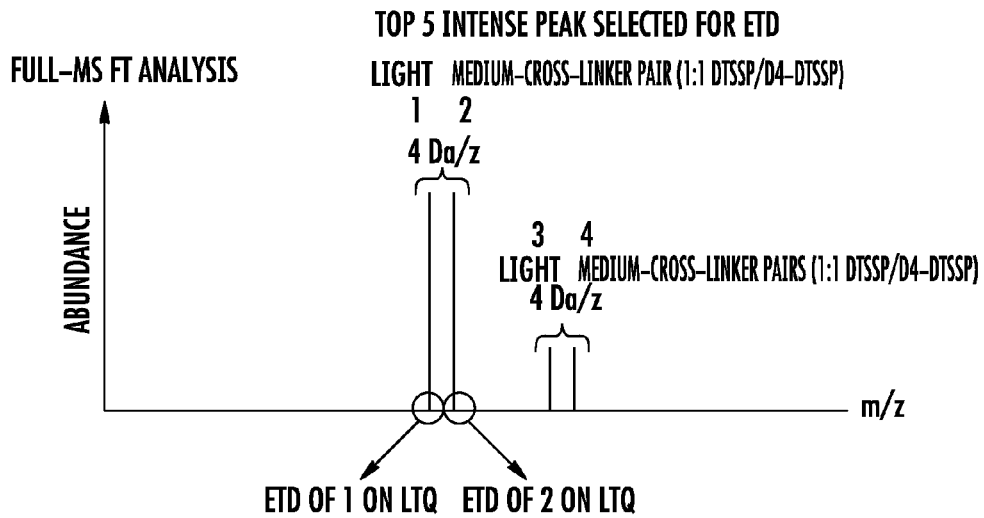
FIGS. 7A to 7C are schematic illustrations of an extended iTIP workflow incorporating DTSSP and d4-DTSSP.
Figure 7B:
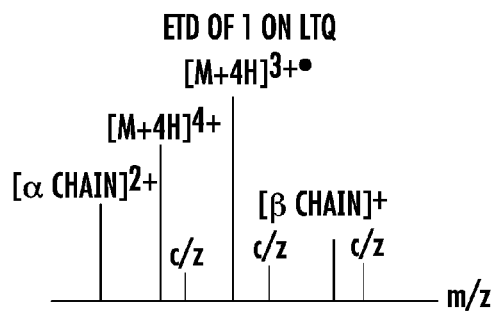
Figure 7C:
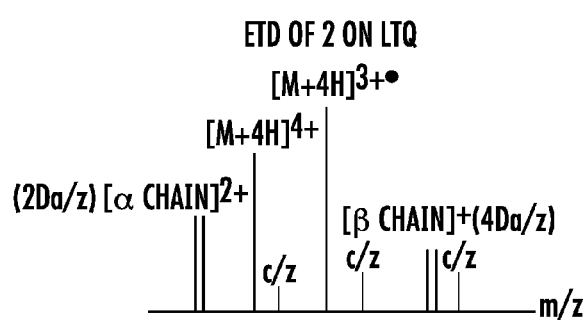

FIGS. 7A to 7C are schematic illustrations of an extended iTIP workflow incorporating DTSSP and d4-DTSSP. FIG. 7A is a typical MS$^1$ spectrum when medium:light cross-linkers (1:1 mole ratio of DTSSP and asymmetric d4-DTSSP) are used, where the cross-linked peptides are observed in MS$^1$ (Full-MS high resolution accurate mass spectrum using FT-fourier transform Orbitrap mass analysis) as doublets peaks 1, 2 and peaks 3, 4 with a Δm of 4 Da/z. FIGS. 7B and 7C show spectra for peaks 1 and 2, respectively, after dissociation via MS$^2$-ET. For d4-DTSSP cross-linker, a constant isobaric mass in seen in MS$^1$ (Peak 2), while the isotopes differences are encoded in the peptide halves after dissociation via MS$^2$-ETD is seen as a doublet of α-chain and doublet of n-chain (FIG. 7C). When a DTSSP cross-linker is used and then subjected to ETD it does not produce a doublet peak as the cross-linker itself is symmetric across the cleavable site (FIG. 7B).

Thus, in some embodiments, a mass spectrometry process is provided, comprising providing a sample to be analyzed, wherein the sample comprises proteins or any molecule that has a primary amine group (NH$_2$-group) that can react with a cross-linker, adding an isotope labeled cross-linker to the sample, wherein the isotope labeled cross-linker comprises an asymmetrically deuterated 3,3'-dithiobis(sulfosuccinimidyl sulfo propionate) molecule, digesting the proteins into peptides, and analyzing the sample using mass spectrometry. In such a process the cross-linker can in some embodiments comprise a 3,3'-dithiobis(sulfosuccinimidyl sulfo propionate) molecule comprising a disulfide bond, and a deuterium label positioned on one side of the disulfide bond of the 3,3'-dithiobis(sulfosuccinimidyl sulfo propionate) molecule, wherein the deuterium label causes the 3,3'-dithiobis(sulfosuccinimidyl sulfo propionate) molecule to be structurally asymmetrical across the disulfide bond. In some embodiments, the cross-linker can comprise the chemical structure illustrated in FIG. 1, wherein b is the disulfide bond, wherein the a-b segment is a protonated light tag that can attach to NH$_2$ of a lysine residue or protein N-terminus during cross-linking, wherein the b-c segment is a deuterated heavy tag that can attach to NH$_2$ of a lysine residue or protein N-terminus during cross-linking.

In some embodiments, a mass spectrometry process as disclosed herein can comprise using a proteolytic enzyme to digest the proteins. In some aspects, analyzing a sample in a mass spectrometry process can comprise analyzing the peptides cross-linked by the cross-linker. In some aspects, such a process can further comprise ionizing the sample using electron spray ionization or matrix-assisted laser desorption ionization.

In some embodiments, a mass spectrometry process as disclosed herein can further comprise selecting a cross-linked peptide from the mass spectrometry analysis, dissociating the disulfide bond on the cross-linker, and analyzing the peptides using tandem mass spectrometry. In some aspects, the dissociation of the disulfide bond comprises the use of electron transfer dissociation. In some aspects, the analysis using tandem mass spectrometry provides spectra with doublet peaks, wherein the doublet peaks represent cross-linked peptides. As discussed herein, one of the doublet peaks can be larger than the other due to the asymmetry of the deuterated cross-linker, wherein the larger doublet peak is the heavy chain and the smaller doublet peak is the light chain. The difference in the mass (Delta Mass) of the peaks can correspond to the mass of the deuterium label on the asymmetrical cross-linker.

In some embodiments, a mass spectrometry process as disclosed herein can further comprise analyzing a doublet peak using collision induced dissociation (CID) or high energy collision dissociation (HCD) mass spectrometry, wherein both the heavy chain and light chain are analyzed. In some embodiments, such a process can further comprise utilizing the results of the mass spectrometry to identify a protein by searching a sequence database or spectral library.

Provided herein are also methods of identifying a protein. Such methods can in some embodiments comprise providing a sample to be analyzed, wherein the sample comprises a protein, adding an isotope labeled cross-linker to the sample, wherein the isotope labeled cross-linker comprises an asymmetrically deuterated 3,3'-dithiobis(sulfosuccinimidyl sulfo propionate) molecule, digesting the protein into peptides, performing serial or tandem mass spectrometry to analyze the sample, and comparing data from the tandem mass spectrometry to a database or spectral library to identify a protein. In some aspects, analyzing the sample comprises analyzing the peptides cross-linked by the cross-linker. In some aspects, the tandem mass spectrometry can comprise electro spray ionization mass spectrometry, intact mass analysis (MS), electron transfer dissociation tandem mass spectrometry (MS/MS), and subsequent collision induced dissociation mass spectrometry (MS/MS/MS). That is, in some aspects, the ETD dissociation reactions are taken to an extra CID step.

Figure 8A:
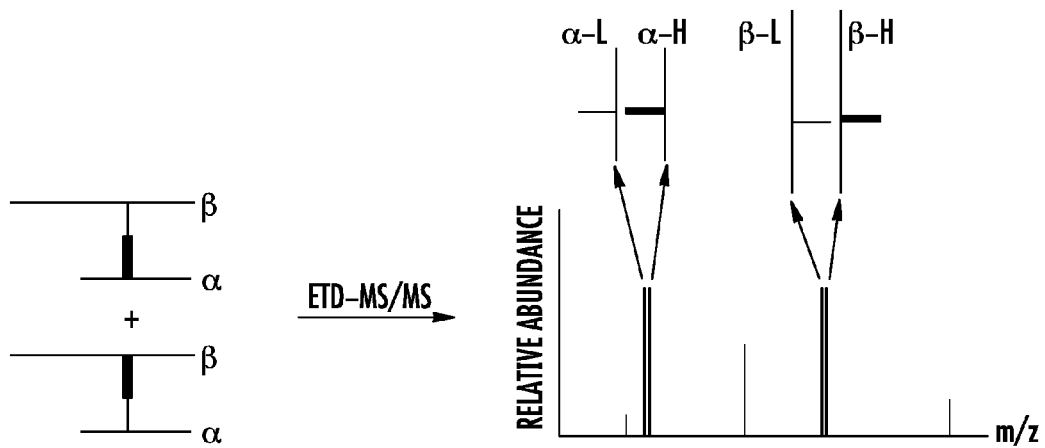
FIGS. 8A to 8D are schematics and spectral illustrations illustrating the ETD-MS/MS results when various combinations of d4-DTSSP cross-linkers are employed.
Figure 8B:
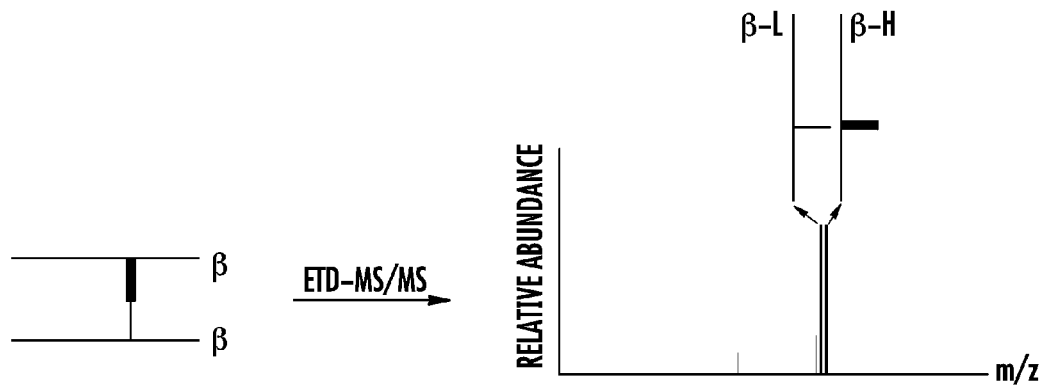
Figure 8C:
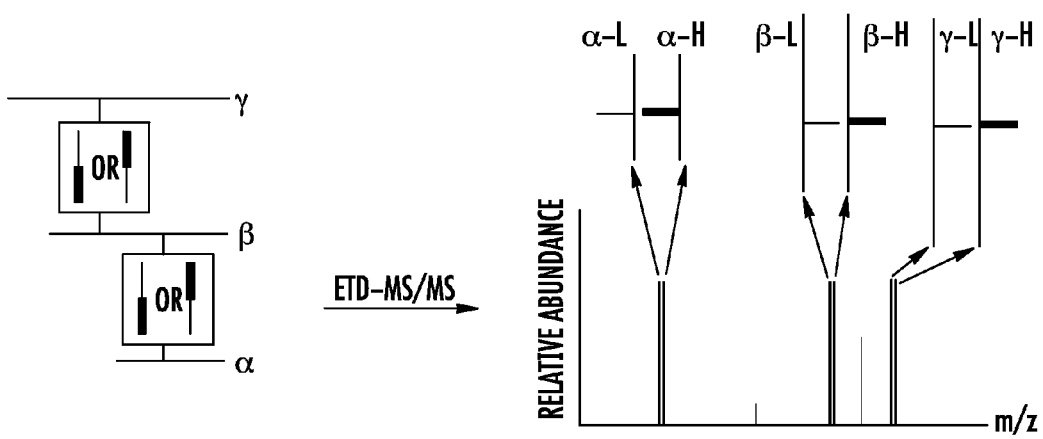
Figure 8D:
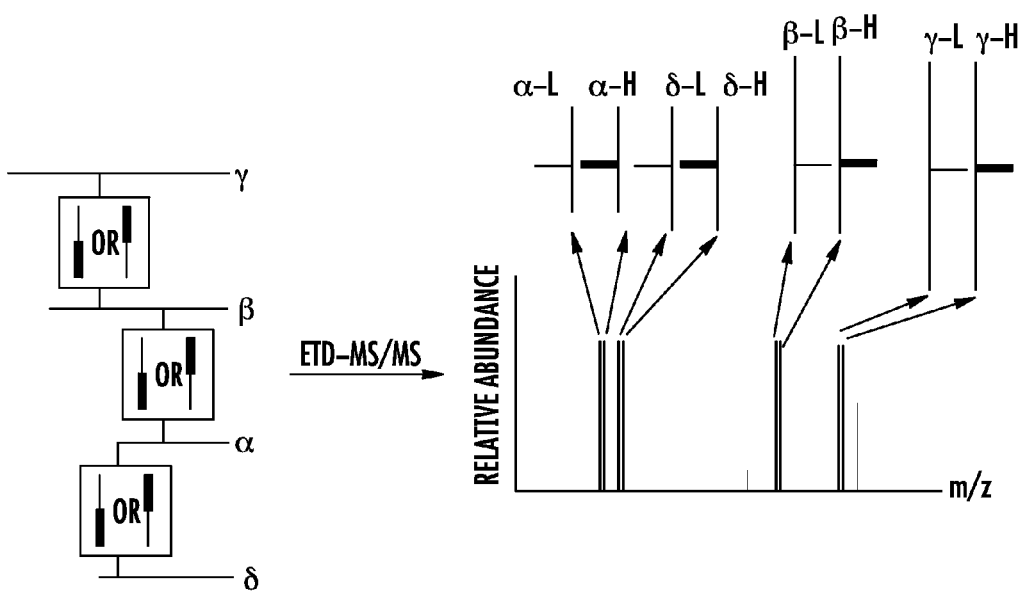

FIGS. 8A-8D illustrate the diverse ways in which a d4-DTSSP cross-linker can be observed in polypeptide backbones derived from post-ETD MS/MS spectra. These possibilities include, for example, intermolecular and intramolecular inter-peptide cross links of various configurations. Additionally, intra-peptide cross-links and dead-end cross-links can also be detected via ETD-based fragmentation. The type of cross-link, and also the configuration of inter-peptides links can be characterized. FIG. 8A shows the typical inter-linked peptides resulting in two constituent chains that differ in size. In particular, FIG. 8A illustrates ETD-MS/MS of hetero dimeric d4-DTSSP cross-linked peptides resulting in two constituent α and β chains that differ in size. The MS/MS spectrum comprised of two distinct doublets of peaks with a characteristic isotopic spacing of 4 Da/z. FIG. 8B shows a possibility of inter-linked peptides that are similar in size and perhaps similar in sequence. In particular, FIG. 8B illustrates ETD-MS/MS of a homo dimeric d4-DTSSP inter-linked peptides that are similar in size and possibly similar in sequence. The MS/MS spectrum is comprised of a single doublet of peaks having the characteristic isotope spacing of 4 Da/z. The peptides generated from multiple cross-links can in some embodiments be more complicated, as shown in FIGS. 8C and 8D, for example. FIG. 8C illustrates ETD-MS/MS possibility of a hetero trimeric peptide cross-linked with two d4-DTSSP inter-linkers and FIG. 8D illustrates a possibility of a hetero quaternary peptide cross-linked with three d4-DTSSP inter-linkers. The MS/MS features in these cases generate more complex patterns. In both spectra, products ions due the cleavage of all inter-linked cross-linkers are depicted by their characteristic doublet. However, there may exist possibilities of a single specific cross-linker cleavage or combination of multiple specific cross-linker-cleavages, as discussed further in the Examples herein.

Figure 9A:
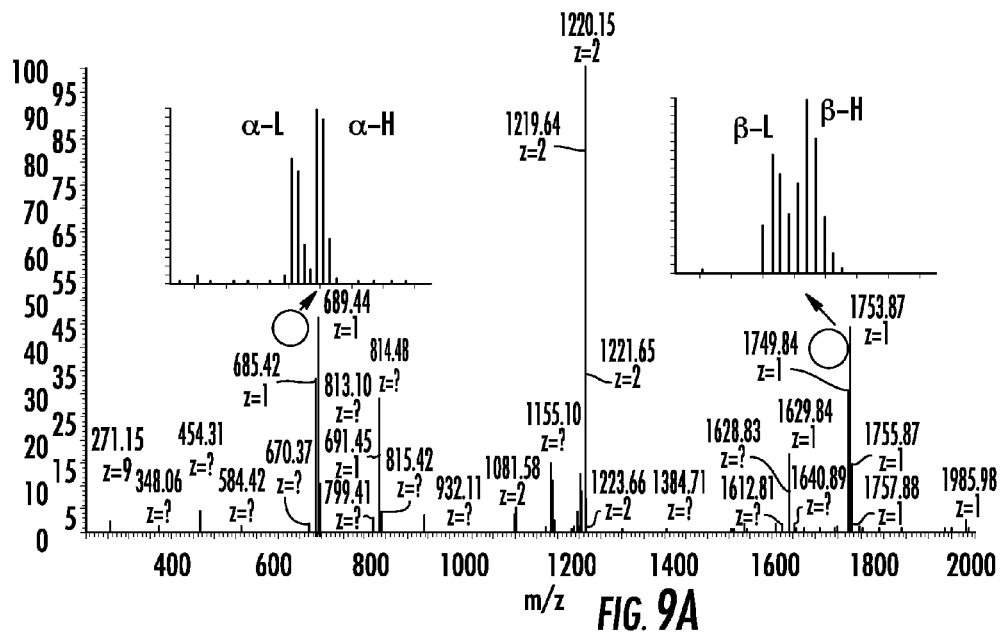
FIGS. 9A to 9B are spectrum from ETD-MS/MS and $CID-MS^3$, respectively.
Figure 9B:
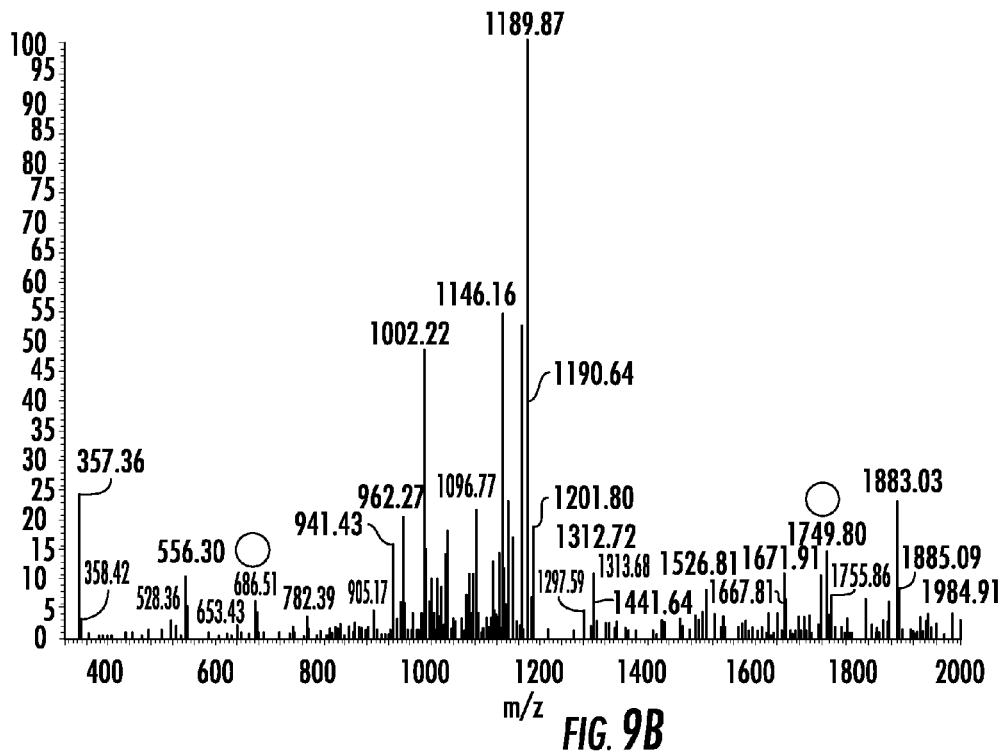

FIGS. 9A to 9B are spectrum from ETD-MS/MS and CID-MS$^3$, respectively, which provide results that demonstrate the strategy of MS$^2$-ETD and isotope tagging of cross-linked peptides. FIG. 9A is an ETD-MS/MS spectrum of polypeptide pairs α/β (hetero dimeric pairs) having different masses interlinked via asymmetric d4-DTSSP. The dissociation of the cross-linker yields the constituent α-L and α-H polypeptide and β-L and β-H polypeptide (see inset). FIG. 9B illustrates that the CID-MS$^3$ of the charge reduced [M+3H]$^{2+\cdot\cdot\cdot}$ peak m/z 1220.15 Da resulted in the generation of minor amounts of the [α-L]$^+$/[α-H]$^+$ and [β-L]$^+$/[β-H]$^+$ product ions. The spectrum is convoluted by CID product ions and c/z ETD product ions of both α/β (hetero dimeric pairs).

FIG. 9A shows ETD-MS/MS of [M+3H]$^{3+}$ precursor ion m/z=814.48 Da, an interlinked cross-linked polypeptide that was derived from d4-DTSSP cross-linking reactions with holomyoglobin. The disulfide cleavage products were the dominant but not the most abundant. Product ions spectrum here comprise of a distribution of charge reduced species [M+3H]$^{3+}$, [M+3H]$^{2+\cdot\cdot\cdot}$, a series of backbone cleavage product ions that gives rise to c- and •z-type ions, and three doublets of fragment ions corresponding to the cleavage of isotope coded disulfide-linked cross-linker. The doublet peaks are indicative of interlinked polypeptides with two chains. The doublet of peaks of m/z: 685.42, and 689.44 have a nominal mass difference of 4 Da corresponding to the ΔM generated by the dissociation across the disulfide of an asymmetric d4-DTSSP cross-linker. Upon close examination of the isotope clusters of both these peaks, an isotope spacing of 1 Da indicates they are singly charged fragment ions. Similarly, the doublet of m/z 1750.7, and 1754.7 has a mass difference of 4 Da with each peak having an isotope spacing of 1 Da. The isotope spacing indicates that of a singly charged fragment that makes up for the ΔM of 4 Da indicative of dissociation across the disulfide bond of an asymmetric d4-DTSSP cross-linker. Both these doublets appear to be complimentary fragments generated via single dissociation of charged reduced radical cations; [M+3H]$^{2+\cdot}$ at the disulfide bond since cleavage resulted in the conservation of the overall charge the radical cation. The constituent peptides chains with their corresponding charge states for doublets pairs are labeled as [α-L]$^+$/[α-H]$^+$ and [β-L]$^{2+}$/[β-H]$^{2+}$.

FIG. 9B shows the CID-MS$^3$ of the charge reduce [M+3H]$^{2+\cdot\cdot\cdot}$ peak m/z 1220.15 Da resulted in the generation of minor amounts of the [α-L]$^+$/[α-H]$^+$ and [β-L]$^+$/[β-H]$^+$ doublet pairs that was indicative that initial ETD step resulted in the facile cleavage of the cross-linker and very minor amount electron transferred yet undissociated cross-linked products exists (ET no D). The spectrum is difficult to interpret since it's a mixture or convolution from both hetero dimeric pairs. The strategy used here was to sequence each α and β components independently via CID.

Figure 10:
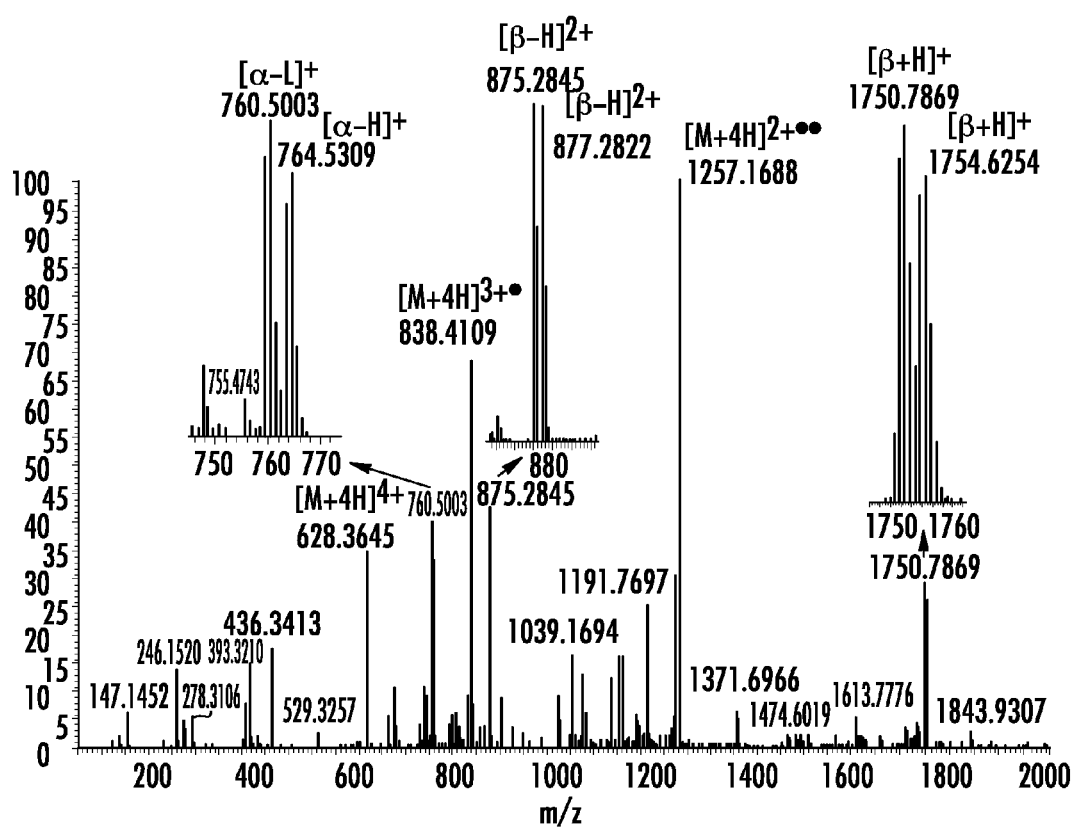
FIG. 10 is an ETD-MS/MS spectrum of a quadruply charged inter-linked peptide resulting from the cross-linking reaction between holomyoglobin and asymmetric d4-DTSSP.

FIG. 10 is an ETD-MS/MS spectrum of a quadruply charged inter-linked peptide resulting from the cross-linking reaction between holomyoglobin and asymmetric d4-DTSSP. The polypeptide pairs α/β (hetero dimeric pairs) having different masses interlinked via asymmetric d4-DTSSP. Insets shows show the dissociation products associated with the cross-linker that is seen as an isotope coded mass tag with each constituent chain labeled as α-L and α-H doublet and β-L and β-H doublet. The dissociation of the cross-linker yields the constituent α-L and α-H polypeptide and β-L and β-H polypeptides. The α-chain is singly charged ([α-L]$^+$/[α-H]$^+$) while the β-chain is doubly charged [β-L]$^{+2}$/[β-H]$^{+2}$ and singly charged [β-L]$^+$/[β-H]$^+$ as shown in the inset, as discussed further in the Examples.

Figure 11A:
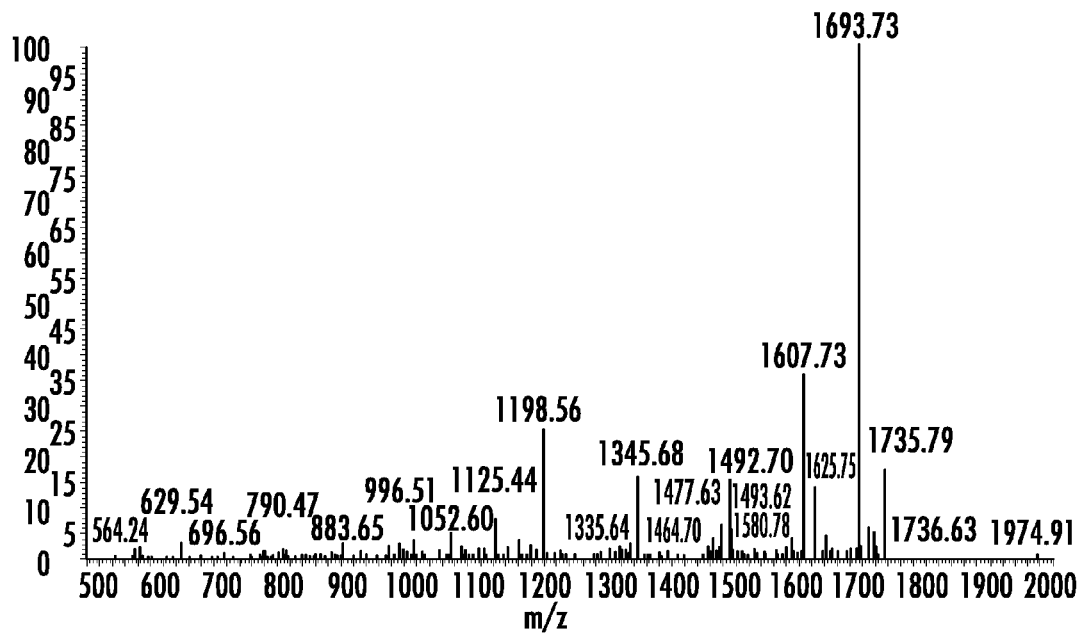
FIGS. 11A to 11B are MS³-CID spectra of polypeptide pairs α/β (hetero dimeric pairs) generated from FIG. 9A.
Figure 11B:
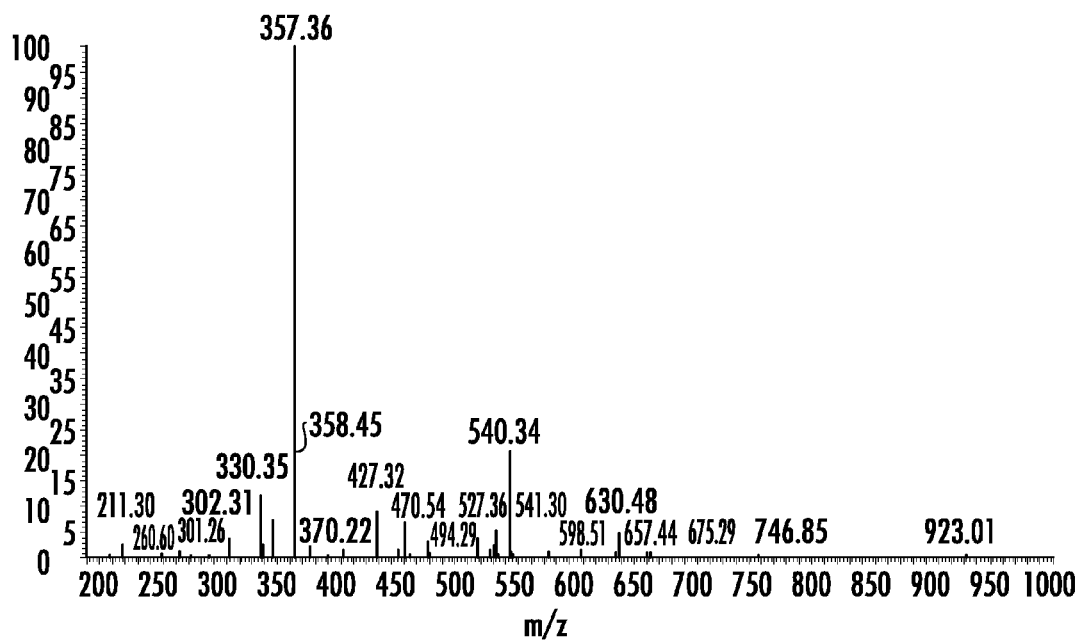
Figure 12:
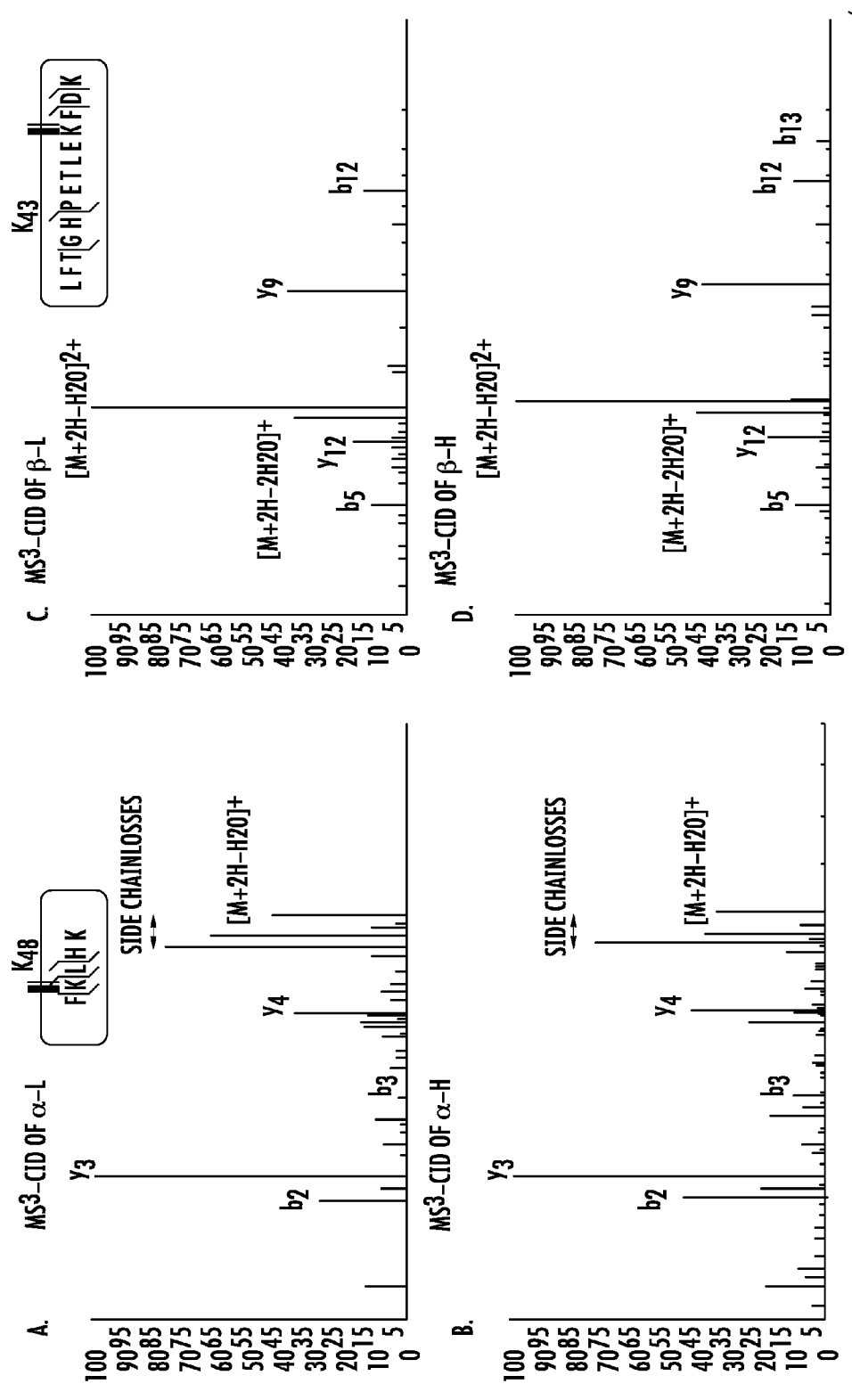
FIGS. 12A to 12D are CID-MS³ spectra of a polypeptide pair α/β (hetero dimeric pairs) generated from FIG. 10. The spectrum from CID-MS³ of α-L (FIG. 12A), α-H (FIG. 12B), β-L (FIG. 12C), and β-H (FIG. 12D) are presented along with the corresponding sequence map of each polypeptide depicting CID fragmentation and location of lysine residues that are cross-linked.

FIGS. 11A to 11B are MS$^3$-CID spectra of polypeptide pairs α/β (hetero dimeric pairs) generated from FIG. 9A. FIG. 11A is a CID spectrum of m/z 1749.8=[β-L]$^+$. FIG. 11B is a CID spectrum of m/z 685.4=[α-L].

In particular, these doublets peaks generated in FIG. 9A and FIG. 10 are structurally interrogated via CID-MS$^3$ and shown in FIGS. 11A-11B and 12A-12D. The iTIP strategy also allows MS$^3$-CID of both heavy/light chains of each peptide sequence providing additional degree of confidence in their identification as interacting proteins or interaction sites within a protein. FIGS. 12A-12D shows the resulting product ions spectra for the α-chain$_L$, α-chain$_H$, β-chain$_L$, and β-chain$_H$ that are the constituent peptide chains of the interacting lysine pair at site of interaction for holomyoglobin. Each type of chain is distinguishable by their respective isotope spacing encoded in L-H4 methylene and H-d4 methylene. The sequence for each constituent polypeptide ion was identified using a database search against Uniprot database and both sequences were identified as sequence of myoglobin. The constituent peptide sequences are referenced back to the MS$^2$-ETD spectrum to make a pair-wise interaction map that shows K43 and K48 (see FIGS. 14 and 15) of myoglobin was cross-linked by d4-DTSSP and the interaction was within a distance of 12 Å (spacer of the cross-linker).

In some embodiments, the disulfide bond of the presently disclosed asymmetric d4-cross-linker (inter-linked to peptides), or any other asymmetric cross-linker disclosed herein, can be subjected to a number of electron or radical mediated dissociation techniques. By way of example and not limitation, electron capture (ECD), 257 nm UV photo dissociation, and/or low temperature plasma of electrospray (ESI) generated ions are few alternative techniques to the electron transfer dissociation (ETD) method for ESI generated cross-linked peptide cations. Additionally, disulfide-linked peptides can be efficiently dissociated at the S—S (disulfide) bond via negative ion collision induced dissociation (neg-CID) and gas-phase ion/ion reactions between gold anions [Au(I)Cl2]-.

In some embodiments, MALDI can lead to peptide backbone fragments analogous to ECD/ETD during the ionization process. When the peptides are mixed with an appropriate MALDI matrix the extent of disulfide bond cleavage can be significant. Thus, in some embodiments cross-linkers disclosed herein can also be subjected to any of the aforementioned ionization and dissociation methods to generate characteristic disulfide bond cleavage products that are easily visualized by a pair of doublet peaks. In some embodiments, in addition to ESI as a method of generating ions and ETD as the first dissociation method, MALDI can be used for generating and electron induced dissociation of the S—S bond of an asymmetric cross-linker, e.g. d4-DTSSP, in one step. Then, cross-linked peptides can be readily identified by their characteristic doublets as disclosed herein. The characteristic doublet peaks can, in some aspects, be further subjected CID-TOF/TOF on a MALDI-TOF/TOF mass spectrometer or Q2-CID (beam-type CID) and Q3-CID (in-trap CID), in a MALDI source implemented on a QTRAP type mass spectrometer that allows for sequence determination.

FIGS. 13A to 13C illustrate the use of disclosed asymmetric cross-linkers in matrix-assisted laser desorption ionization (MALDI) mass spectrometry. FIG. 13A is a schematic illustrating a MALDI mass spectrometry method for electron-induced dissociation of d4-DTSSP dead-end cross-linker peptides P1 and P2, using a MALDI spotting strategy that alternates between rows for spotting either sinapinic acid as the matrix in row 1 or 1,5-DAN as the matrix in row 2 (Note that peptides fraction in B13 and B14 are similar. FIG. 13B is a graphic illustrating a MALDI plate spotted via an LC spotter. FIG. 13C is a full MS spectrum of intact peptides in Spot B13 and Full-MS spectrum of dissociated cross-linked peptides derived from Spot B14.

In some embodiments, an asymmetric cross-linker as disclosed herein, e.g., d4-DTSSP, can be used to identify and/or characterize protein-drug interactions. For example, in some embodiments a disclosed cross-linker can be used for protein-drug interaction studies such as affinity pull-down of protein complexes using small molecule inhibitor drugs. The field popularly known as chemical proteomics allows screening for putative specific interactors of the target protein (or bait protein) that also binds with a small molecule drug. As disclosed herein, a cross-linker can be used in the context of chemical proteomics experiments to directly map the interaction site of the bait protein with the small molecule provided that the small molecule drug contains at least a primary amine that can be cross-linked. Additionally, in some embodiments a disclosed cross-linker can also be used to verify off-target binding of a drug using the cross-linker to detect non-bait proteins associated with the small molecule drug.

Figure 17:
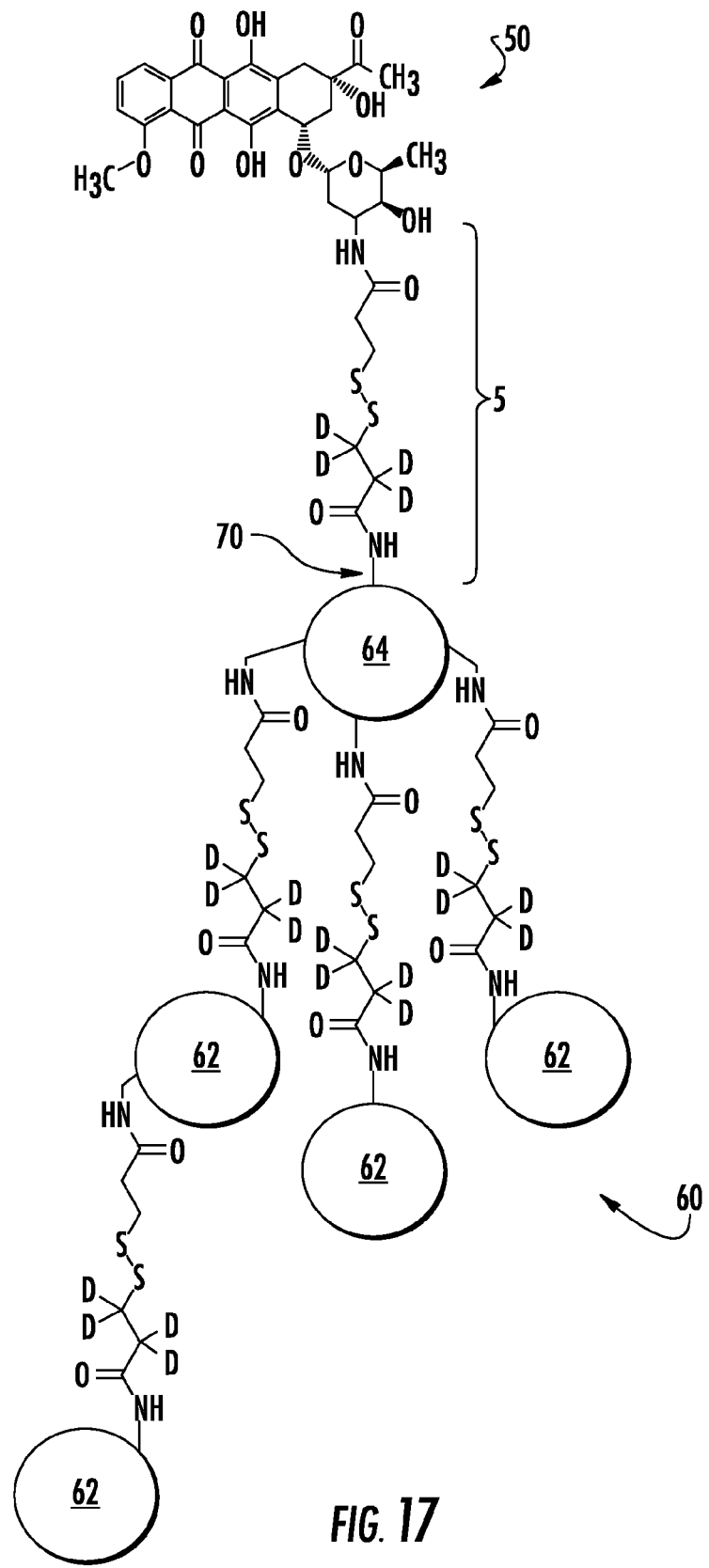
FIG. 17 is a schematic illustration of a cross-linker used to define a protein-drug interaction.

As depicted in FIG. 17, a cross-linker 5 can be used to characterize an interaction between a drug 50, such as for example a DNA intercalating drug, and an interacting protein complex 60. Interacting protein complex 60 can comprise a plurality of proteins 62 and in some aspects a bait protein 64. Cross-linker 5 can interact with the amine groups on drug 50 and bait protein 64. Such an interaction can be analyzed using a mass spectrometry based analysis workflow as disclosed herein to characterize an interaction between a drug and a protein, and/or identify a protein to which a drug interacts, and vice versa. A protein-cross-linked drug 70 can then be identified.

EXAMPLES

The following Examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods for Examples 1-7

Materials

All chemicals and solvents were of the highest grade and used without further purification. 3-Mercaptopropionic acid, 2,2'-dithiodipyridine and dimethylformamide (DMF) were purchased from Acros. Dicyclohexylcarbodimide (DCC) and ethanol were purchased from Sigma-Aldrich. N-Hydroxysulfosuccinimide sodium salt (NHSS) was purchased from Fluka. Acetic acid and ethyl acetate were purchased from Fisher Scientific. 2,2',3,3'-Tetradeuterium-3-mercaptopropanoic acid was purchased from Creative Molecules Inc.

Synthesis of Asymmetric d4-DTSSP and Other Asymmetric Linkers

Asymmetric d4-DTSSP, illustrated in FIG. 1, and other asymmetric linkers are synthesized as disclosed herein. A disulfide, tetrahydrofuran, water and 2,2',3,3'-Tetradeuterium-3-mercaptopropanoic acid can be mixed, as illustrated in FIG. 2. The resultant compound in dimethylformamide can be mixed with N-hydroxysulfosuccinimide sodium salt and dicyclohexylcarbodiimide. A cross linker can then be obtained after a series of centrifugations.

Asymmetric d4-DTSSP, as illustrated in FIG. 1, can comprise amine reactive sites a and c, and an ETD cleavable site b. The synthetic product, asymmetric d4-DTSSP, was fully characterized by NMR $^1$H NMR (CDCl$_3$, 400 MHz) δ 3.11-3.15 (m, 2H), 3.19-3.26 (m, 4H), 3.40 (d, J=9.2 Hz, 1H), 3.44 (d, J=9.6 Hz, 1H), 4.33 (d, J=8.8 Hz, 1H), 4.52 (d, J=8.8 Hz, 1H).

Asymmetric d4-DTSSP can in some embodiments be extended to any desired length, using for example, starting materials selected from the group consisting of 6-mercaptohexanoic acid, 8-mercaptooctonoic acid, and/or 4-mercaptobutyric acid. Synthesis of asymmetric linkers as disclosed herein of different linker lengths can in some embodiments enable the determination of distances or interaction space between or within a protein.

Protein Cross-Linking and Proteolysis

Protein cross-linking was carried out on ubiquitin and holomyoglobin using a manufacturer's protocol described for DTSSP cross-linkers (Pierce Inc.). The protein solution was buffer exchanged to ABC and trypsinized in a 3M spin-filter device (Millipore inc.). Peptides were desalted using PepClean columns.

Mass Spectrometry Analysis

Data dependent LC-MS/MS was carried out on a LTQ-Orbitrap mass spectrometer coupled to Eksigent 2D nano ultra LC system (Gunawardena et al., 2011). The targeted experiments comprising ETD-MS/MS were followed by at a minimum two CID-MS/MS scans or two high energy collision dissociation (HCD)-MS/MS scans for each polypeptide light/heavy chains. Mass spectra were processed by filtering MS$^3$-CID or -HCD spectra and peptide identification was performed on filtered spectra by MASCOT (Matrix Science Inc.) against a human-IPI database (V3.63). Peptides were confidently identified using a target-decoy approach (Elias et al., 2007; Weatherly et al., 2005), with a 1% false discovery rate (FDR). A precursor ion mass tolerance of 100 ppm and a product ion mass tolerance 0.5 Da were used during the initial search with a maximum of two missed trypsin cleavages. Variable modifications included methionine oxidation and customized cross-linker modifications: d4-S, d4-SH, d4-S, d4-SH at lysine and N-terminus. All search results were filtered for precursor masses to be within a 6 ppm mass accuracy.

Example 1

Rationale for Cross-Linker Design and Isotope Tagging of Interacting Proteins (iTIP) Strategy Provided herein are ETD cleavable cross-linkers comprising a disulfide bond, which can be, among other things, used in studying inter-linked polypeptides in cross-linking-based tandem mass spectrometry experiments. Current disulfide containing cross-linkers such as DTSSP and DSP and their deuterated analogs are structurally symmetrical across the disulfide bond, with a two-fold symmetry, allowing each constituent peptide chains to result in identical mass-tags in ETD-MS$^2$ spectra. The structure of an exemplary asymmetric d4-DTSSP cross-linker as disclosed herein, and as illustrated in FIG. 1, comprises a mass off-set or (m=4 Da) around the S—S bond. The bidirectional orientation of the cross-linker facilitates two fragments in the ETD spectrum for each constituent chain by tagging of heavy c-b segments or light a-b segments (see FIG. 1) of the cross-linker to an amine group of a N-terminus or lysine residue of a peptide via acylation chemistry and the subsequent ETD cleavage of cross-linker at position b of the S—S bond.

FIG. 3A shows the ETD product ion spectrum of inter-linked polypeptide resulting from a cross-linking reaction of Ubiquitin and DTSSP. The product ions consist of mainly α and β chains that are single isotope clusters resulting from the direct cleavage of the DTSSP disulfide bond. FIG. 3B shows the ETD product ion spectrum of the same constituent polypeptide chains inter-linked with an asymmetric d4-DTSSP as disclosed herein. The product ion spectrum looks quite similar to FIG. 3A. However, due to the asymmetry on either sides of the S—S bond, and due to the bidirectional orientation of cross-linkers during the cross-linker reaction step, a doublet of peaks was observed for both α and β chains that are labeled as α-L/α-H and β-L and β-H. Such cross-linkers with asymmetric labeling can be analytically useful as they encode isotopic tags of cross-linked product ions to be readily distinguished from other cleavages due to dissociation of the cross-linker resulting in two distinct fragment ions for each constituent peptide chain and contain a specific mass signature that is observed as a doublet of peaks in the MS$^2$ spectrum.

FIG. 10 shows ETD-MS/MS of [M+4H]$^{4+}$ precursor ion m/z=628.3 Da a interlinked cross-linked polypeptides that was derived from d4-DTSSP cross-linking reactions with holomyoglobin. Unlike FIG. 3A, where disulfide cleavage products were the dominant peaks, the product ions spectrum here comprise of a distribution of charge reduced species [M+4]$^{3+•}$, [M+4]$^{2+••}$, a series of backbone cleavage product ions that gives rise to c- and •z-type ions, and three doublets of fragment ions corresponding to the cleavage of isotope coded disulfide-linked cross-linker. The doublet peaks are indicative of interlinked polypeptides with two chains. The doublet of peaks of m/z: (759.4 and 763.4 monoisotopic mass (A)) 760.5 and 764.5 (A+1; see FIG. 10) have a nominal mass difference of 4 Da corresponding to the ΔM generated by the dissociation across the disulfide of an asymmetric d4-DTSSP cross-linker. Upon close examination of the isotope clusters of both these peaks, an isotope spacing of 1 Da indicates they are singly charged fragment ions. Similarly, the doublet of m/z: 875.2 and 877.2 are separated by a mass difference of 2 Da with each peak having an isotope spacing of 0.5 Da. The isotope spacing indicates that of a doubly charged fragment that makes up for ΔM of 4 Da indicative of dissociation across the disulfide bond of an asymmetric d4-DTSSP cross-linker. Both these doublets appear to be complimentary fragments generated via single dissociation of charged reduced radical cations; [M+4]$^{3+•}$ at the disulfide bond since cleavage resulted in the conservation of the overall charge the radical cation. The constituent peptides chains with their corresponding charge states for doublets pairs are labeled as [α-L]$^+$/[α-H]$^+$ and [β-L]$^{2+}$/[β-H]$^+$. Further, the doublet of m/z 1750.7 and 1754.7 has a mass difference of 4 Da with each peak having an isotope spacing of 1 Da, again indicating singly charged fragments corresponding to the isotope coded product ions of the cross-linker. The generation of these doublet peaks [β-L]$^+$/[β-H]$^+$ are believed to be due to the sequential charge reduction of doubly charged doublets [β-L]$^{2+}$/[β-H]$^{2+}$. The iTIP approach readily generated diagnostic ions that can be structurally interrogated to obtain their identities via CID that is more suitable for doubly and singly charged peptides.

Example 2

Synthesis of Asymmetric d4-DTSSP and Other Asymmetric Linkers

A disulfide (16.9 mg, 79 μmol), tetrahydrofuran (THF; 0.4 mL), H$_2$O (0.3 mL) and 2,2',3,3'-Tetradeuterium-3-mercaptopropanoic acid (83 μL, 1 M in D$_2$O, 83 μmol) was added successively to a vial at room temperature. The reaction mixture was stirred for 1 hr and then concentrated under reduced pressure. Flash chromatography (CH$_2$Cl$_2$: MeOH=95:5 with 0.4% formic acid) over silica gel gave 3-((2-carboxyethyl)disulfanyl)propanoic-2,2,3,3d$_4$ acid as white solid (9.3 mg, 55%). To a solution of 3-((2-carboxyethyl)disulfanyl)propanoic-2,2,3,3-d$_4$ acid (4.3 mg, 20 μmol) in dimethylformamide (DMF; 0.3 mL) was added N-hydroxysulfosuccinimide sodium salt (NHSS; 8.7 mg, 40 μmol) and dicyclohexylcarbodiimide (DCC; 8.3 mg, 40 μmol) successively at room temperature. The resulting solution was stirred for 4 hrs and then subjected to centrifuge. The supernatant was collected and 1.2 mL of ethyl acetate was added. The resulting mixture was centrifuged. The precipitate was collected and washed by ethyl acetate three times. After drying by SpeedVac the cross-linker was obtained as a pale white solid (7.0 mg, 57%).

Referring to FIG. 2, 3-mercaptopropanoic acid (C$_3$H$_6$O$_2$S; MW 106.14) A and 1,2-di(pyridine-2-yl)disulfane (C$_{10}$H$_8$N$_2$S$_2$; MW 220.31) B can be mixed with an acid (such as AcOH) and an alcohol (such as EtOH) at room temperature in step 1 to yield 3-(pyridine-2-yldisulfanyl) propanoic acid (C$_8$H$_9$NO$_2$S$_2$; MW 215.29) C. The mixing can in some embodiments take place for about 16 hours (hr). In step 2 3-(pyridine-2-yldisulfanyl)propanoic acid C can be mixed with 2,2',3,3'-Tetradeuterium-3-mercaptopropanoic acid D in DMF and H$_2$O (1:1) at room temperature to yield 3-((2-carboxyethyl)disulfanyl)propanoic-2,2,3,3-d$_4$ acid E. The mixing can in some embodiments take place for about 1 hr. In step 3, 3-((2-carboxyethyl)disulfanyl)propanoic-2, 2,3,3-d$_4$ acid E can be mixed in DMF with NHSS and DCC at room temperature to yield sodium 1-((3-((3-((2,5-dioxo-3-sulfonatopyrrolidin-1-yl)oxy)-3-oxopropyl)disufanyl)propanoyl-2,2,3,3-d$_4$)oxy)-2,5-dioxyopyrrolidine-3-sulfonate F (also referred to as d4-DTSSP). The mixing in step 3 can be at room temperature for about 4 hours.

Asymmetric d4-DTSSP F, as illustrated in FIGS. 1 and 2, comprises amine reactive sites a and c (FIG. 1), and an ETD cleavable site b (FIG. 1). The synthetic product, asymmetric d4-DTSSP F, was fully characterized by NMR $^1$H NMR (CDCl$_3$, 400 MHz) δ 3.11-3.15 (m, 2H), 3.19-3.26 (m, 4H), 3.40 (d, J=9.2 Hz, 1H), 3.44 (d, J=9.6 Hz, 1H), 4.33 (d, J=8.8 Hz, 1H), 4.52 (d, J=8.8 Hz, 1H).

Asymmetric d4-DTSSP, as illustrated in FIG. 1, can in some embodiments be extended to any desired length. Starting materials can be used in conjunction with their completely deuterated forms (via H/D exchange process) to synthesize various linker lengths of asymmetric cross-linkers as described herein. By way of example and not limitation, such starting materials can comprise 6-mercaptohexanoic acid, 8-mercaptooctonoic acid, and/or 4-mercaptobutyric acid. Synthesis of asymmetric linkers as disclosed herein of different linker lengths can in some embodiments enable the determination of distances or interaction space between or within a protein.

By way of example and not limitation, a linker that is longer than asymmetric-d4 DTSSP by two carbon bond lengths can be synthesized using 4-mercaptobutyric acid as a starting material. A resulting linker can comprise an asymmetric d6-cross-linker.

By way of example and not limitation, a linker that is longer than DTSSP by six carbon bond lengths can be synthesized using 6-mercaptohexanoic acid as a starting material. A resulting linker can comprise an asymmetric d10-cross-linker.

By way of example and not limitation, a linker that is longer than DTSSP by ten carbon bond lengths can be synthesized using 8-mercaptohexanoic acid as a starting material. A resulting linker can comprise an asymmetric d14-cross-linker.

Example 3

Nomenclature for Cross-Linking Peptide Diversity and iTIP Recognition

FIGS. 8A-8D show the diverse ways in which a d4-DTSSP cross-linker can be observed in polypeptide backbones derived from post-ETD MS/MS spectra. These possibilities include, for example, intermolecular and intramolecular inter-peptide cross links of various configurations. Additionally, intra-peptide cross-links and dead-end cross-links can also be detected via ETD-based fragmentation. The type of cross-link, and also the configuration of inter-peptides links can be characterized. FIG. 8A shows the typical inter-linked peptides resulting in two constituent chains that differ in size. The MS/MS spectrum comprised of two distinct doublets of peaks, sometime that are also the most abundant, with a characteristic isotopic spacing of 4 Da/z. FIG. 8B shows a possibility of inter-linked peptides that are similar in size and perhaps similar in sequence. The MS/MS spectrum is comprised of a single doublet of peaks having the characteristic isotope spacing of 4 Da/z. Inter-peptide cross-linked peptides with a single disulfide bond can in some embodiments be structurally most useful since they can in some instances be easier to interpret.

The peptides generated from multiple cross-links can in some embodiments be more complicated, as shown in FIGS. 8C and 8D, for example. In both spectra, products ions due the cleavage of all inter-linked cross-linkers are depicted by their characteristic doublet. However, there may exist possibilities of a single specific cross-linker cleavage or combination of multiple specific cross-linker-cleavages. For example, the peptide shown in FIG. 8C may have two more permutations leading to dissociation products [α+β] and [β+γ] chain. Likewise, peptides in FIG. 8D can in some embodiments have five additional permutations resulting in dissociation products [α+β+γ], [δ+α+β], [α+β], [δ+α], [β+γ] chains. The dead-end cross linkers are easier to detect since ETD dissociation of the disulfide bond can lead to a neutral loss of product ions forming yet again a doublet. The neutral loss is generally the hydrolyzed cross-linked product.

Example 4

Results Demonstrating the Strategy of MS$^2$-ETD and Isotope Tagging of Cross-Linked Peptides FIG. 9A shows ETD-MS/MS of [M+3H]$^{3+}$ precursor ion m/z=814.48 Da, an interlinked cross-linked polypeptide that was derived from d4-DTSSP cross-linking reactions with holomyoglobin. The disulfide cleavage products were the dominant but not the most abundant. Product ions spectrum here comprise of a distribution of charge reduced species [M+3H]$^{3+}$, [M+3H]$^{2+\bullet}$, a series of backbone cleavage product ions that gives rise to c- and •z-type ions, and three doublets of fragment ions corresponding to the cleavage of isotope coded disulfide-linked cross-linker. The doublet peaks are indicative of interlinked polypeptides with two chains. The doublet of peaks of m/z: 685.42, and 689.44 have a nominal mass difference of 4 Da corresponding to the ΔM generated by the dissociation across the disulfide of an asymmetric d4-DTSSP cross-linker. Upon close examination of the isotope clusters of both these peaks, an isotope spacing of 1 Da indicates they are singly charged fragment ions. Similarly, the doublet of m/z 1750.7, and 1754.7 has a mass difference of 4 Da with each peak having an isotope spacing of 1 Da. The isotope spacing indicates that of a singly charged fragment that makes up for the ΔM of 4 Da indicative of dissociation across the disulfide bond of an asymmetric d4-DTSSP cross-linker. Both these doublets appear to be complimentary fragments generated via single dissociation of charged reduced radical cations; [M+3H]$^{2+\bullet}$ at the disulfide bond since cleavage resulted in the conservation of the overall charge the radical cation. The constituent peptides chains with their corresponding charge states for doublets pairs are labeled as [α-L]$^+$/[α-H]$^+$ and [β-L]$^{2+}$/[β-H]$^{2+}$.

FIG. 9B shows the CID-MS$^3$ of the charge reduce [M+3H]$^{2+\bullet}$ peak m/z 120.15 Da resulted in the generation of minor amounts of the [α-L]$^+$/[α-H]$^+$ and [β-L]$^+$/[β-H]$^+$ doublet pairs that was indicative that initial ETD step resulted in the facile cleavage of the cross-linker and very minor amount electron transferred yet undissociated cross-linked products exists (ET no D). The spectrum is difficult to interpret since it's a mixture or convolution from both hetero dimeric pairs. The strategy used here was to sequence each α and β components independently via CID.

FIG. 10 shows ETD-MS/MS of [M+4H]$^{4+}$ (example of a quadruply charged cross-linked polypeptide) precursor ion m/z=628.3 D, an inter-linked cross-linked polypeptide that was derived from d4-DTSSP cross-linking reactions with holomyoglobin. Unlike FIG. 9A, where disulfide cleavage products were the dominant peaks, the product ions spectrum here comprise distribution of charge reduced species [M+4]$^{3+\bullet}$, [M+4]$^{2+\bullet\bullet}$, a series of backbone cleavage product ions that gives rise to c- and •z-type ions, and three doublets of fragment ions corresponding to the cleavage of isotope coded disulfide-linked cross-linker. The doublet peaks are indicative of interlinked polypeptides with two chains. The doublet of peaks of m/z: 759.4, and 763.4 have a mass difference of 4 Da corresponding to the ΔM generated by the dissociation across the disulfide of an asymmetric d4-DTSSP cross-linker. Upon close examination of the isotope clusters of both these peaks, shows an isotope spacing 1 Da indicating they are singly charged fragment ions. Similarly, the doublet of m/z: 875.2, and 877.2 are separated by a mass difference of 2 Da with each peak having an isotope spacing of 0.5 Da. The isotope spacing indicates that of a doubly charged fragment that makes up for ΔM of 4 Da indicative of dissociation across the disulfide bond of an asymmetric d4-DTSSP cross-linker. Both these doublets are believed to be complimentary fragments generated via single dissociation of charged reduced radical cations; [M+4]$^{3+\bullet}$ at the disulfide bond since cleavage resulted in the conservation of the overall charge the radical cation. The constituent peptides chains with their corresponding charge states for doublets pairs are labeled as [α-L]⁺/[α-H]⁺ and [β-L]²⁺/[β-H]²⁺. Further, the doublet of m/z 1750.7 and 1754.7 has a mass difference of 4 Da with each peak having an isotope spacing of 1 Da, again indicate a singly charged fragments corresponding to the isotope coded product ions of the cross-linker. The generation of these doublet peaks [β-L]⁺/[β-H]⁺ are believed to be due to the sequential charge reduction of doubly charged doublets [β-L]²⁺/[β-H]²⁺. The iTIP approach readily generated diagnostic ions regardless of their abundance. These ions are structurally interrogated to obtain their identities via CID. The selection of these peaks for CID would not be feasible if these ion signatures were absent.

Example 5

Identification of Interaction Peptide Pairs

These doublets peaks generated in FIG. 9A and FIG. 10 are structurally interrogated via CID-MS³ and shown in FIGS. 11A-11B and 12A-12D. The iTIP strategy also allows MS³-CID of both heavy/light chains of each peptide sequence providing additional degree of confidence in their identification as interacting proteins or interaction sites within a protein. FIGS. 12A-12D shows the resulting product ions spectra for the α-chain$_L$, α-chain$_H$, β-chain$_L$, and β-chain$_H$ that are the constituent peptide chains of the interacting lysine pair at site of interaction for holomyoglobin. Each type of chain is distinguishable by their respective isotope spacing encoded in L-H4 methylene and H-d4 methylene. The sequence for each constituent polypeptide ion was identified using a database search against Uniprot database and both sequences were identified as sequence of myoglobin. The constituent peptide sequences are referenced back to the MS²-ETD spectrum to make a pair-wise interaction map that shows K43 and K48 of myoglobin was cross-linked by d4-DTSSP and the interaction was within a distance of 12 Å (spacer of the cross-linker).

FIGS. 11A to 11B are MS³-CID spectra of polypeptide pairs α/β (hetero dimeric pairs) generated from FIG. 7A. FIG. 11A is a CID spectrum of m/z 1749.8=[β-L]⁺. FIG. 11B is a CID spectrum of m/z 685.4=[α-L].

FIGS. 12A to 12D are CID-MS³ spectra of a polypeptide pair α/β (hetero dimeric pairs) generated from FIG. 10. The spectrum from CID-MS³ of α-L (FIG. 12A), α-H (FIG. 12B), β-L (FIG. 12C), and β-H (FIG. 12D) are presented along with the corresponding sequence map of each polypeptide depicting CID fragmentation and location of lysine residues that are cross-linked.

Example 6 d4-Asymmetric Cross-Linker Analysis by MALDI

The disulfide bond of the presently disclosed asymmetric d4-cross-linker (inter-linked to peptides), or any other asymmetric cross-linker disclosed herein, can be subjected to a number of electron or radical mediated dissociation techniques. By way of example and not limitation, electron capture (ECD), 257 nm UV photo dissociation, and/or low temperature plasma of electrospray (ESI) generated ions are few alternative techniques to the electron transfer dissociation (ETD) method for ESI generated cross-linked peptide cations. Additionally, disulfide-linked peptides can be efficiently dissociated at the S—S (disulfide) bond via negative ion collision induced dissociation (neg-CID) and gas-phase ion/ion reactions between gold anions [Au(I)Cl2]-.

In some embodiments, MALDI can lead to peptide backbone fragments analogous to ECD/ETD during the ionization process. When the peptides are mixed with an appropriate MALDI matrix the extent of disulfide bond cleavage can be significant. Thus, in some embodiments cross-linkers disclosed herein can also be subjected to any of the aforementioned ionization and dissociation methods to generate characteristic disulfide bond cleavage products that are easily visualized by a pair of doublet peaks.

To illustrate this, MALDI in-source electron induced dissociation methods were applied towards the systematic analysis of d4-assymetric cross-linked peptides via a MALDI spotting strategy that uses two-types of matrix molecules that can either: 1) preserve the disulfide linkage during ionization; or 2) selectively dissociate the disulfide linkage during ionization, of cross-linked polypeptides. The same LC fractions were introduced to two consecutive rows on the plate that was pre-spotted with 3,5-dimethoxy-4-hydroxycinnamicc acid as the matrix that preserves and 1,5-diaminonaphthalene (1,5-DAN) as the matrix that induces electron induced dissociation during laser irradiation.

FIGS. 13A to 13C illustrate the use of disclosed asymmetric cross-linkers in matrix-assisted laser desorption ionization (MALDI) mass spectrometry. FIG. 13A is a schematic illustrating a MALDI mass spectrometry method for electron-induced dissociation of d4-DTSSP dead-end cross-linker peptides P1 and P2, using a MALDI spotting strategy that alternates between rows for spotting either sinapinic acid as the matrix in row 1 or 1,5-DAN as the matrix in row 2 (Note that peptides fraction in B13 and B14 are similar. FIG. 13B is a graphic illustrating a MALDI plate spotted via an LC spotter. FIG. 13C is a full MS spectrum of intact peptides in Spot B13 and Full-MS spectrum of dissociated cross-linked peptides derived from Spot B14.

The pair-wise spotting method allows the cross-linked fragments ions to be assigned to their constituent intact cross-linked peptide masses. In the example shown in FIG. 13C spot B14 (top spectrum) consists of peptides P1 and P2 dead-end cross-linkers that are identified readily via a dominant doublet peaks (α-L, α-H) and (β-L, β-H). Unlike the ETD experiment where peptides were mass selected before fragmentation, here all ions are subjected to electron induced dissociation during MALDI. FIG. 13C shows the corresponding intact dead-end cross-linked peptides P1 and P2 of MALDI ions generated at spot B13 (bottom spectrum).

This demonstrates that in addition to ESI as a method of generating ions and ETD as the first dissociation method, MALDI can be used for generating and electron induced dissociation of the S—S bond of an asymmetric cross-linker, e.g. d4-DTSSP, in one step. Then, cross-linked peptides can be readily identified by their characteristic doublets as disclosed herein. The characteristic doublet peaks can, in some aspects, be further subjected CID-TOF/TOF on a MALDI-TOF/TOF mass spectrometer or Q2-CID (beam-type CID) and Q3-CID (in-trap CID), in a MALDI source implemented on a QTRAP type mass spectrometer that allows for sequence determination.

Example 7 d4-Asymmetric Cross-Linker Analysis Using Myoglobin

Horse heart myoglobin (SEQ ID NO. 1) was exposed to a d4-asymmetric cross-linker as disclosed herein. As depicted in FIGS. 14A-14D at two cross-linking sites. In particular, cross-linker 5 interacted with lysine (K) residues between peptide 10 (SEQ ID NO. 2) and peptide 20 (SEQ ID NO. 3), see FIGS. 14A and 14B, and between peptide 10 (SEQ ID NO. 2) and peptide 30 (SEQ ID NO. 4), see FIGS. 14A and 14C. Cross-linker 5 also linked a heme group 7 to peptide 10 (SEQ ID NO. 2), as depicted in FIG. 14D.

SEQ ID NO. 1 of FIG. 15A shows lysine residues K43 and K48 that were cross-linked in Myoglobin. The constituent peptide sequences are referenced back to the $MS^2$-ETD spectrum to make a pair-wise interaction map that shows K43 and K48 of myoglobin was cross-linked by d4-DTSSP and the interaction was within a distance of 12 Å (spacer of the cross-linker). This was derived from the analysis of FIGS. 10 and 12 for one of the interactions and the sequence represents the interaction map (FIG. 15).

Cleavage of cross-linker 5 resulted in ion products depicted in FIGS. 15B-15E. Particularly, FIG. 15B depicts the $α_L$-chain (peptide 20; SEQ ID NO. 3); FIG. 15C depicts the $α_H$-chain (peptide 20; SEQ ID NO. 3); FIG. 15D depicts the $β_L$-chain (peptide 10; SEQ ID NO. 2); and FIG. 15E depicts the $β_H$-chain (peptide 10; SEQ ID NO. 2).

Figure 14:
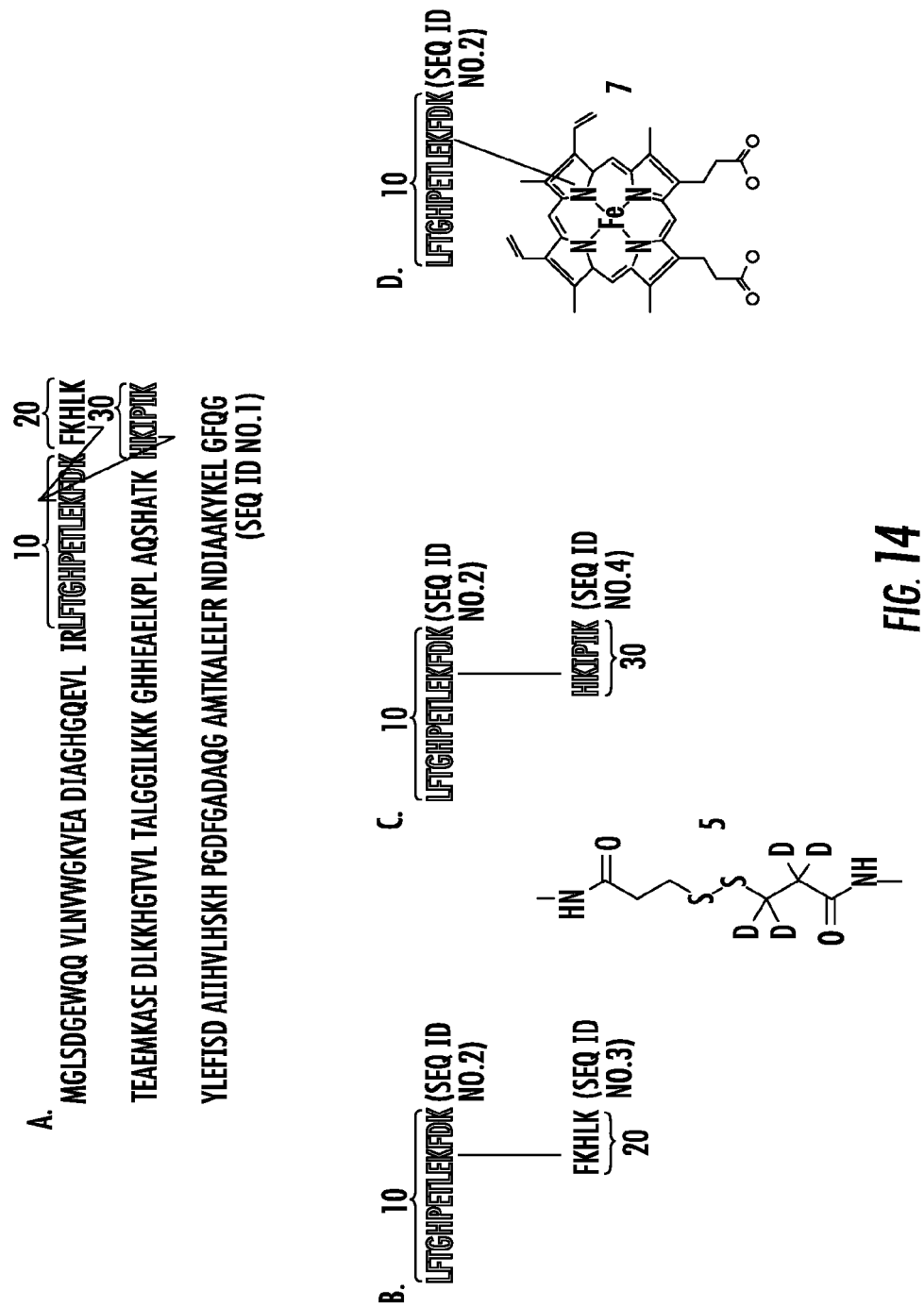
FIGS. 14A to 14D are schematic illustrations of cross-linker interactions with peptides in horse heart myoglobin.

FIG. 14 shows all the other cross-linking possibilities of K43 (SEQ ID NO. 2) that is cross-linked to another remote Lysine (K99) and also the heme group 7 which is a non-peptide entity.

Proteome analysis can be conducted using a workflow as depicted in FIG. 6A, for example. In particular, an exemplary search workflow illustrating the filtration and search of ion spectra data using both SEQUEST and MASCOT search engines is illustrated in FIG. 6A. Spectrum files 100 can in some embodiments be selected using spectrum selector 200 and filtered using scan event filter 300 and related scan-filtering procedures, and can be searched using MASCOT 400 or SEQUEST 500 search engines and compared against a protein sequence data base to identify the peptide. FIG. 16 is an exemplary output from a search using a search engine, which identifies the peptide fragments of FIGS. 15B-15E. In some embodiments, identified proteins can be validated using peptide validator 600.

REFERENCES

1. Gunawardena, H. P.; Huang, Y.; Kenjale, R.; Wang, H.; Xie, L.; Chen, X., Unambiguous characterization of site-specific phosphorylation of leucine-rich repeat Fli-I-interacting protein 2 (LRRFIP2) in Toll-like receptor 4 (TLR4)-mediated signaling. *J Biol Chem* 2011, 286, (13), 10897-910.
2. Elias, J. E.; Gygi, S. P., Target-decoy search strategy for increased confidence in large-scale protein identifications by mass spectrometry. *Nat Methods* 2007, 4, (3), 207-14.
3. Weatherly, D. B.; Atwood, J. A., 3rd; Minning, T. A.; Cavola, C.; Tarleton, R. L.; Orlando, R., A Heuristic method for assigning a false-discovery rate for protein identifications from MASCOT database search results. *Mol Cell Proteomics* 2005, 4, (6), 762-72.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An isotope labeled amine reactive cross-linker, comprising:
   a 3,3'-dithiobis(sulfosuccinimidyl sulfo propionate) molecule comprising a disulfide bond; and
   a deuterium label positioned on one side of the disulfide bond of the 3,3'-dithiobis(sulfosuccinimidyl sulfo propionate) molecule, wherein the deuterium label causes the 3,3'-dithiobis(sulfosuccinimidyl sulfo propionate) molecule to be structurally asymmetrical across the disulfide bond, wherein the disulfide bond can be dissociated, wherein dissociation of the disulfide bond creates a first and a second cleavage product, wherein one of the first or second cleavage products comprises the deuterium label, wherein the first and a second cleavage products differ in mass, and wherein the nominal mass of the cleavage products differs by 4 Daltons.

2. The cross-linker of claim 1, wherein the deuterium label is on a methylene carbon of the 3,3'-dithiobis(sulfosuccinimidyl sulfo propionate) molecule.

3. The cross-linker of claim 1, comprising the following chemical structure:

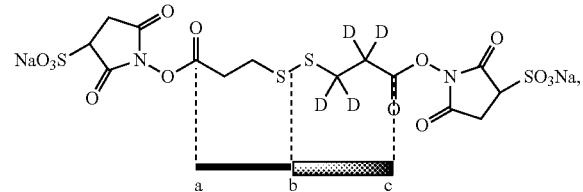

wherein b is the disulfide bond, wherein the a-b segment is a protonated light tag that can attach to NH$_2$ of a lysine residue or protein N-terminus during cross-linking, wherein the b-c segment is a deuterated heavy tag that can attach to NH$_2$ of a lysine residue or protein N-terminus during cross-linking.

4. An isotope labeled amine reactive cross-linker, comprising:
   a 3,3'-dithiobis(sulfosuccinimidyl sulfo propionate) molecule comprising a disulfide bond; and
   a deuterium label positioned on one side of the disulfide bond of the 3,3'-dithiobis(sulfosuccinimidyl sulfo propionate) molecule, wherein the deuterium label causes the 3,3'-dithiobis(sulfosuccinimidyl sulfo propionate) molecule to be structurally asymmetrical across the disulfide bond,
   wherein the cross-linker comprises the following chemical structure:

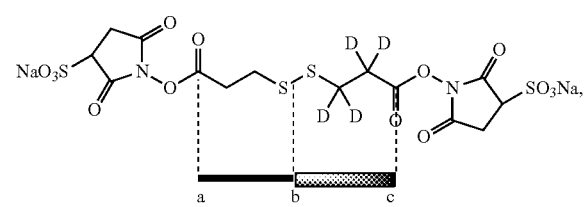

wherein b is the disulfide bond, wherein the a-b segment is a protonated light tag that can attach to NH$_2$ of a lysine residue or protein N-terminus during cross-linking, wherein the b-c segment is a deuterated heavy tag that can attach to NH$_2$ of a lysine residue or protein N-terminus during cross-linking.

* * * * *

SEQUENCE LISTING

```
<160> NUMBER OF SEQ ID NOS: 4

<210> SEQ ID NO 1
<211> LENGTH: 154
<212> TYPE: PRT
<213> ORGANISM: Equus caballus

<400> SEQUENCE: 1

Met Gly Leu Ser Asp Gly Glu Trp Gln Gln Val Leu Asn Val Trp Gly
1               5                   10                  15

Lys Val Glu Ala Asp Ile Ala Gly His Gly Gln Glu Val Leu Ile Arg
            20                  25                  30

Leu Phe Thr Gly His Pro Glu Thr Leu Glu Lys Phe Asp Lys Phe Lys
        35                  40                  45

His Leu Lys Thr Glu Ala Glu Met Lys Ala Ser Glu Asp Leu Lys Lys
    50                  55                  60

His Gly Thr Val Val Leu Thr Ala Leu Gly Gly Ile Leu Lys Lys Lys
65                  70                  75                  80

Gly His His Glu Ala Glu Leu Lys Pro Leu Ala Gln Ser His Ala Thr
                85                  90                  95

Lys His Lys Ile Pro Ile Lys Tyr Leu Glu Phe Ile Ser Asp Ala Ile
            100                 105                 110

Ile His Val Leu His Ser Lys His Pro Gly Asp Phe Gly Ala Asp Ala
        115                 120                 125

Gln Gly Ala Met Thr Lys Ala Leu Glu Leu Phe Arg Asn Asp Ile Ala
    130                 135                 140

Ala Lys Tyr Lys Glu Leu Gly Phe Gln Gly
145                 150
```

```
<210> SEQ ID NO 2
<211> LENGTH: 14
<212> TYPE: PRT
<213> ORGANISM: Equus caballus

<400> SEQUENCE: 2

Leu Phe Thr Gly His Pro Glu Thr Leu Glu Lys Phe Asp Lys
1               5                   10

<210> SEQ ID NO 3
<211> LENGTH: 5
<212> TYPE: PRT
<213> ORGANISM: Equus caballus

<400> SEQUENCE: 3

Phe Lys His Leu Lys
1               5

<210> SEQ ID NO 4
<211> LENGTH: 6
<212> TYPE: PRT
<213> ORGANISM: Equus caballus

<400> SEQUENCE: 4

His Lys Ile Pro Ile Lys
1               5
```